(12) United States Patent
Fujiwara

(10) Patent No.: US 9,176,090 B2
(45) Date of Patent: Nov. 3, 2015

(54) SENSOR CHIP, AND MEASUREMENT DEVICE AND BLOOD TEST DEVICE IN WHICH THIS SENSOR CHIP IS USED

(75) Inventor: Masaki Fujiwara, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 338 days.

(21) Appl. No.: 13/258,641

(22) PCT Filed: Mar. 17, 2010

(86) PCT No.: PCT/JP2010/001909
§ 371 (c)(1),
(2), (4) Date: Sep. 22, 2011

(87) PCT Pub. No.: WO2010/116624
PCT Pub. Date: Oct. 14, 2010

(65) Prior Publication Data
US 2012/0010486 A1   Jan. 12, 2012

(30) Foreign Application Priority Data

Apr. 7, 2009  (JP) .................................. 2009-092630

(51) Int. Cl.
G01N 21/77       (2006.01)
G01N 31/22       (2006.01)
(Continued)

(52) U.S. Cl.
CPC ............ *G01N 27/26* (2013.01); *A61B 5/1411* (2013.01); *A61B 5/1486* (2013.01); *A61B 5/14532* (2013.01); *A61B 5/157* (2013.01); *A61B 5/150022* (2013.01); *A61B 5/150099* (2013.01); *A61B 5/15113* (2013.01); *A61B 5/15134* (2013.01); *A61B 5/15138* (2013.01); *A61B 5/150213* (2013.01); *A61B 5/150274* (2013.01); *A61B 5/150358* (2013.01); *G01N 27/3272* (2013.01); *A61B 5/15174* (2013.01); *G01N 35/1016* (2013.01); *G01N 2035/1062* (2013.01)

(58) Field of Classification Search
None
See application file for complete search history.

(56) References Cited

U.S. PATENT DOCUMENTS

| 4,540,492 A | 9/1985 | Kessler |
| 5,609,749 A | 3/1997 | Yamauchi et al. |

(Continued)

FOREIGN PATENT DOCUMENTS

| EP | 1 593 961 | 11/2005 |
| JP | 7-234201 | 9/1995 |

(Continued)

OTHER PUBLICATIONS

International Search Report issued Jun. 22, 2010 in International (PCT) Application No. PCT/JP2010/001909.

(Continued)

*Primary Examiner* — Jill Warden
*Assistant Examiner* — Brittany Fisher
(74) *Attorney, Agent, or Firm* — Wenderoth, Lind & Ponack, L.L.P.

(57) ABSTRACT

This sensor chip (11) comprises a substrate (15) in the form of a flat board, a sample inlet (20) that is provided in the thickness direction of the substrate (15) and into which flows the blood (3) used for measurement, a supply path (21) that communicates with this sample inlet (20), and detection electrodes (17, 18, 19) provided to this supply path (21), wherein the substrate (15) is provided with a surplus blood reservoir (25) that draws in surplus blood (3a) and holds this drawn surplus blood (3a).

33 Claims, 24 Drawing Sheets

(51) Int. Cl.
*G01N 27/26* (2006.01)
*A61B 5/15* (2006.01)
*A61B 5/145* (2006.01)
*A61B 5/1486* (2006.01)
*A61B 5/151* (2006.01)
*A61B 5/157* (2006.01)
*G01N 27/327* (2006.01)
*G01N 35/10* (2006.01)

(56) References Cited

U.S. PATENT DOCUMENTS

| | | | |
|---|---|---|---|
| 6,551,838 B2 * | 4/2003 | Santini, Jr. | A61B 5/00 422/504 |
| 6,607,644 B1 * | 8/2003 | Apffel, Jr. | 204/451 |
| 7,012,017 B2 * | 3/2006 | Brunner et al. | 438/613 |
| 7,785,271 B2 | 8/2010 | Fujiwara et al. | |
| 8,000,762 B2 | 8/2011 | Calasso et al. | |
| 8,162,854 B2 | 4/2012 | Calasso et al. | |
| 8,206,318 B2 * | 6/2012 | Uchiyama et al. | 600/583 |
| 8,221,336 B2 * | 7/2012 | Fujiwara et al. | 600/584 |
| 2005/0123443 A1 | 6/2005 | Fujiwara et al. | |
| 2006/0243589 A1 | 11/2006 | Doi et al. | |
| 2006/0258959 A1 | 11/2006 | Sode | |
| 2006/0293611 A1 | 12/2006 | Calasso et al. | |
| 2007/0038149 A1 | 2/2007 | Calasso et al. | |
| 2007/0161076 A1 | 7/2007 | Halden | |
| 2008/0312518 A1 | 12/2008 | Jina et al. | |
| 2009/0071847 A1 | 3/2009 | Edelbrock et al. | |
| 2010/0286562 A1 | 11/2010 | Fujiwara et al. | |
| 2011/0257493 A1 | 10/2011 | Calasso et al. | |
| 2012/0174688 A1 | 7/2012 | Calasso et al. | |

FOREIGN PATENT DOCUMENTS

| | | |
|---|---|---|
| JP | 10-33507 | 2/1998 |
| JP | 2005-110712 | 4/2005 |
| JP | 2009-22675 | 2/2009 |
| WO | 2004/072632 | 8/2004 |
| WO | 2005/084545 | 9/2005 |
| WO | 2007/133457 | 11/2007 |

OTHER PUBLICATIONS

Supplementary European Search Report issued Oct. 5, 2012 in European Application No. EP 10 76 1332.

* cited by examiner (a)

(b)

US 9,176,090 B2

SENSOR CHIP, AND MEASUREMENT DEVICE AND BLOOD TEST DEVICE IN WHICH THIS SENSOR CHIP IS USED

TECHNICAL FIELD

The present invention relates to a sensor chip for measuring blood glucose, etc., and to a measurement device and a blood test device in which this sensor chip is used.

BACKGROUND ART

A conventional sensor chip, as well as a blood test method in which this sensor chip is used, will now be described.

Diabetes patients must periodically measure their blood glucose, inject insulin based on this blood glucose value, and thereby keep their blood glucose at the proper level at all times. To this end, a patient collects a small amount of blood from a fingertip or the like, and measures the blood glucose from this collected blood. A sensor chip 1 (see FIG. 43) is required to measure the blood glucose.

The sensor chip 1 has a base unit 2, a sample inlet 4, a supply path (not shown), a detection electrode 4b provided to this supply path, and an air hole 4c provided at the very end of the supply path. The base unit 2 is in the form of a flat board having a substantially rectangular shape. The sample inlet 4 is provided to one of the short sides of this base unit 2, and this is where blood 3 flows in for measurement. The supply path communicates with this sample inlet 4. The detection electrode 4b is provided to this supply path. The air hole 4c is provided at the very end of the supply path.

In a blood test method in which this sensor chip 1 is used, first a puncture device 5 is brought into contact with the skin 6 of a finger 6a or the like, as shown in FIG. 44. In this state, a puncture button 5a of the puncture device 5 is depressed. Depressing the puncture button 5a punctures the finger 6a (the skin 6). After this, as shown in FIG. 45, pressure is applied around the punctured finger 6a (skin 6) to squeeze out the blood 3.

Then, as shown in FIG. 46, a measurement device 7 to which this sensor chip 1 is mounted is used to measure the blood glucose. Specifically, the sample inlet 4 of the sensor chip 1 is brought into contact with the blood 3 that was squeezed out. The blood 3 is introduced through the supply path to the detection electrode 4b. The glucose value of the blood 3 introduced to the detection electrode 4b is measured, and this result is displayed on a display component 7a. Insulin is then injected in an amount determined on the basis of this blood glucose value.

In the measurement of blood glucose, a little extra blood 3 is usually squeezed out in order to prevent measurement failure or the like that would otherwise be caused by an inadequate amount of the blood 3. As a result, surplus blood 3a is not used in measurement, and is left on the skin. The remaining surplus blood 3a should not be left that way for both hygienic and safety reasons. Thus, a tissue 8a, cotton ball (not shown), or the like must be separately readied as shown in FIG. 47, and this tissue 8a or cotton ball 8b used to wipe away the surplus blood 3a.

Patent Literature 1, for example, is known as prior art publication information related to the invention in this application.

CITATION LIST

Patent Literature

Patent Literature 1: Japanese Laid-Open Patent Application 2005-110712

SUMMARY

This conventional method, however, entails the following troublesome work.

To wipe away the surplus blood 3a, the user has to carry around the tissue 8a, cotton ball 8b, or the like. Furthermore, the user has to carry around the tissue 8a, cotton ball 8b, or the like that is smeared with the surplus blood 3a after the wiping. Thus carrying around the tissue 8a, cotton ball 8b, or the like in order to wipe away the surplus blood 3a is undesirable in terms of both the hygiene and the safety of the user, and this procedure is bothersome.

The present invention was conceived in view of this, and it is an object thereof to provide a sensor chip with which surplus blood can be dealt with more easily.

To achieve this object, the sensor chip of the present invention is a sensor chip for analyzing the components of a biological sample, comprising a flat substrate, a sample inlet, a supply path, a detection electrode, and a surplus blood reservoir. The sample inlet is provided to one end of the substrate, and the biological sample used for analysis flows in through this inlet. The supply path communicates with the sample inlet, and the biological sample is introduced. Detection electrodes are provided to the supply path and detect signals used for analysis. A surplus blood reservoir is provided to the substrate, and extra blood not used for analysis is drawn and held therein.

The measurement device of the present invention is a measurement device that makes use of the above-mentioned sensor chip, comprising a housing, a sensor insertion portion, a connector, and a measurement circuit. The sensor insertion portion is provided to a first end of the housing, and the sensor chip is inserted therein. The connector is provided to the sensor insertion portion. The measurement circuit is connected to the connector. The display component is connected to the output of the measurement circuit and displays the result of measuring analysis data for a biological sample introduced to the sensor chip and measured with the measurement circuit.

The blood test device of the present invention is a device that makes use of the above-mentioned sensor chip, comprising a housing, a sensor insertion portion, puncture component, a connector, an electrical circuit, and a display component. The sensor insertion portion is provided to part of the housing, and the sensor chip is inserted therein. The puncture component is provided at or near a location that is opposite the sensor insertion portion, and punctures the skin. The connector is provided to the sensor insertion portion. The electrical circuit is connected to the connector and performs analysis of a biological sample. The display component is connected to the output of the electrical circuit.

DESCRIPTION OF EMBODIMENTS

Embodiment 1

Figure 1:
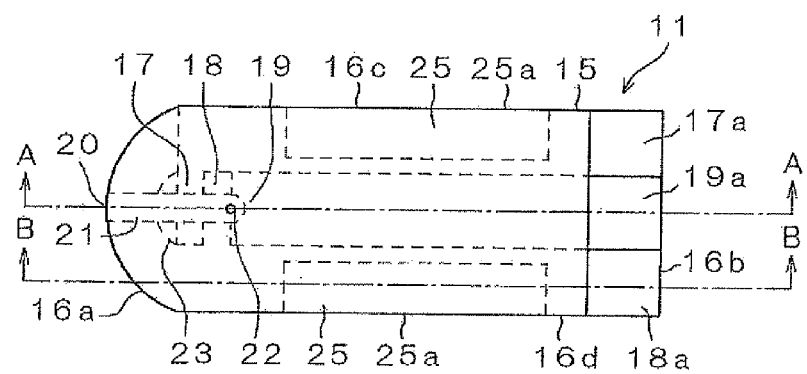
FIG. 1 is a plan view of the sensor chip pertaining to Embodiment 1 of the present invention.
Figure 2:
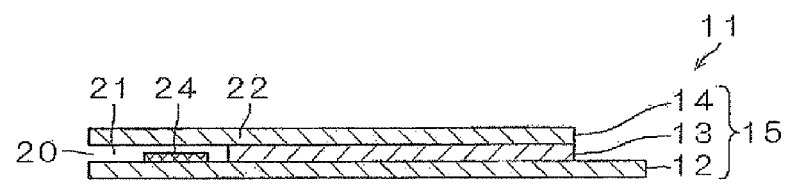
FIG. 2 is an A-A cross section of FIG. 1.
Figure 3:
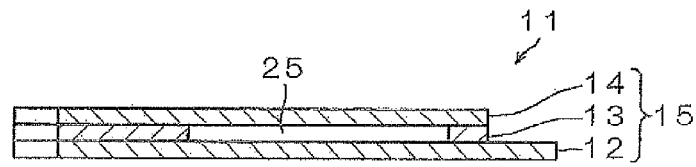
FIG. 3 is a B-B cross section of FIG. 1.

FIG. 1 is a plan view of the sensor chip 11 in Embodiment 1. FIG. 2 is an A-A cross section of FIG. 1, and FIG. 3 is a B-B cross section of FIG. 1. In FIGS. 1, 2, and 3, the sensor chip 11 is in the form of a flat board. As shown in FIGS. 2 and 3, the sensor chip 11 has a three-layer structure that includes a base plate 12, a spacer 13 that is affixed over this base plate 12, and a cover 14 that is affixed over this spacer 13. In other words, the flat base plate 12, the spacer 13, and the cover 14 form a substrate 15.

Also, as shown in FIG. 1, the sensor chip 11 is substantially rectangular, and one short side 16a has a semicircular shape. Detection electrodes 17, 18, and 19 are provided on the base plate 12. The detection electrodes 17, 18, and 19 are formed extending toward the other short side 16b of the sensor chip 11, and are connected to connection terminals 17a, 18a, and 19a, respectively.

Figure 43:
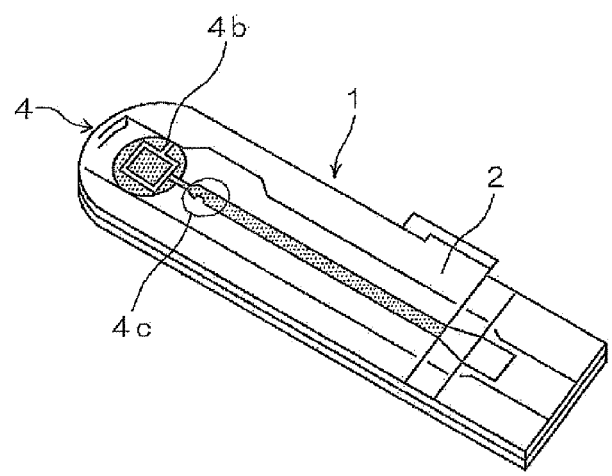
FIG. 43 is a diagram of a conventional sensor chip.
Figure 44:
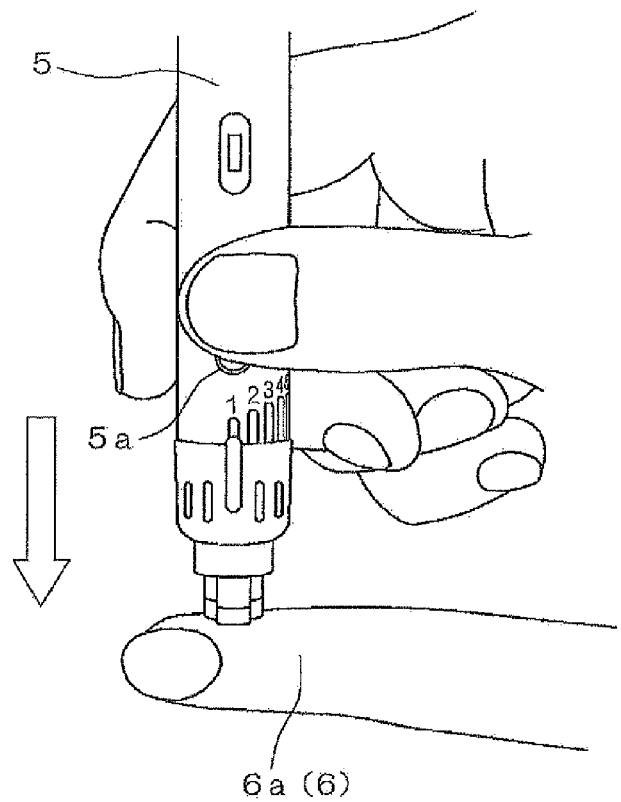
FIG. 44 is a diagram of puncturing with a conventional puncture device.
Figure 45:
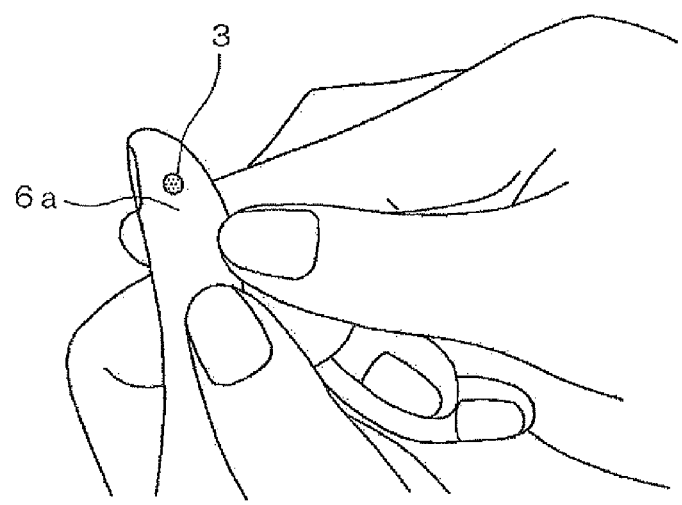
FIG. 45 shows how the blood is squeezed out after puncturing with a conventional puncture device.
Figure 46:
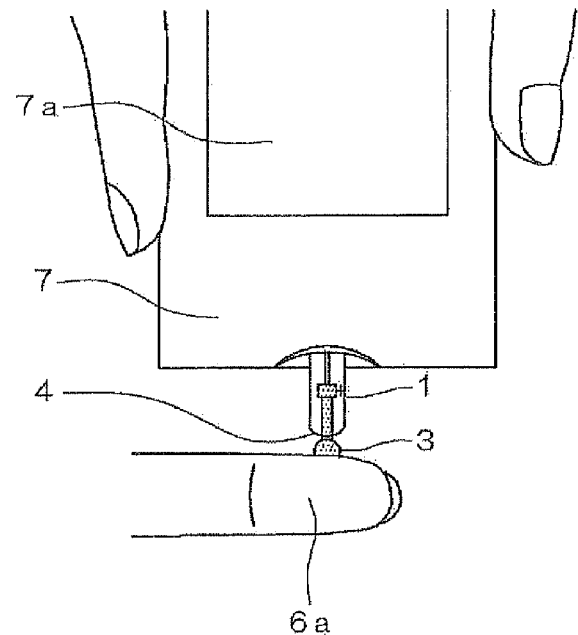
FIG. 46 shows how a drop of the blood that has been squeezed out is applied to the sensor chip mounted in a conventional measurement device.
Figure 47:
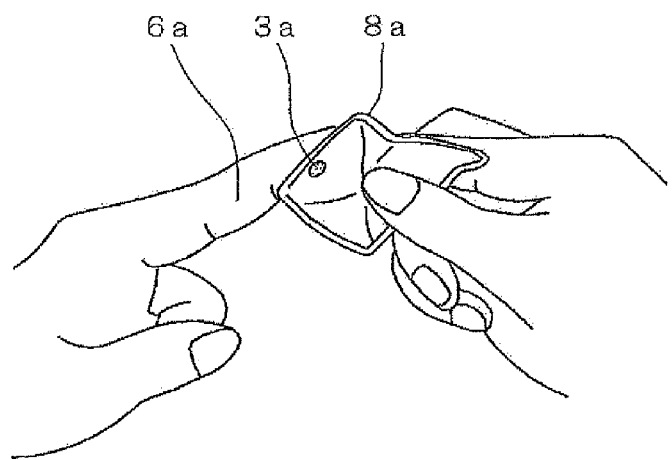
FIG. 47 is an oblique view of post-processing after conventional puncture.

An inlet 20, into which measurement-use blood 3 (see FIGS. 30, 43, and 44) flows, is provided to the distal end of the short side 16*a*. A supply path (capillary) 21 for the measurement-use blood 3 is provided from this inlet 20 toward the other short side 16*b*.

An air hole 22 is provided to the very end of the supply path 21. The detection electrodes 17, 18, and 19 constituting a detector 23 are disposed on the supply path 21. A reagent 24 (see FIG. 5) is placed on the detector 23.

The reagent 24 is produced by adding 0.1 to 5.0 U/sensor of PQQ-GDH, 10 to 200 mM of potassium ferricyanide, 1 to 50 mM of maltitol, and 20 to 200 mM of taurine to a 0.01 to 2.0 wt % CMC aqueous solution, melting the components to prepare a reagent solution, then dropping this onto the detection electrodes 17, 18, and 19 constituting the detector 23, and drying.

Surplus blood reservoirs 25 (see FIGS. 1 and 3) are provided on one long side 16*c* (on top in FIG. 1) and the other long side 16*d* (on the bottom in FIG. 1) of the sensor chip 11.

The surplus blood reservoirs 25 hold surplus blood that remains on the surface of the skin, without being used for blood glucose measurement, out of the blood that has flowed onto the skin surface after puncture. The surplus blood reservoirs 25 each have a surplus blood inlet 25*a* into which surplus blood 3*a* flows. The surplus blood inlets 25*a* communicate with the spaces serving as the surplus blood reservoirs 25.

Also, the surplus blood reservoirs 25 form tiny gaps just as with the supply path 21 discussed above, and the blood 3 (the biological sample to be analyzed) flows in under capillary action. The volume of the surplus blood reservoirs 25 is at least three times the volume of the supply path 21. Therefore, even if more surplus blood 3*a* remains than there is blood used for measurement and analysis, all of the surplus blood 3*a* can be easily and reliably held in the surplus blood reservoirs 25 merely by touching the surplus blood inlets 25*a* on the side faces of the sensor chip 11 to the surplus blood 3*a*.

The inlet 20 and the surplus blood inlets 25*a* are separately provided at different positions. That is, the inlet 20 is provided on the short side 16*a* of the sensor chip 11 (the left side in FIG. 1), whereas the surplus blood inlets 25*a* are provided on the long sides 16*c* and 16*d* of the sensor chip 11 (the top and bottom in FIG. 1). Therefore, when the measurement-use blood 3 is made to flow into the inlet 20, it will not accidentally flow into the surplus blood inlets 25*a*. Thus, even though this sensor chip 11 is provided with the surplus blood inlets 25*a*, the proper amount of blood 3 can be made to flow to the detector 23.

As discussed above, the sensor chip 11 in this embodiment comprises the surplus blood reservoirs 25. Consequently, after the user has introduced the blood 3 through the inlet 20, any surplus blood 3*a* can be held in the surplus blood reservoirs 25 via the surplus blood inlet 25*a* formed on the long side 16*c* or the long side 16*d* of the sensor chip 11. Therefore, the user does not need to carry around a tissue 8*a*, cotton ball 8*b*, or the like as in the past. Furthermore, once the surplus blood 3*a* has been drawn in, the soiled sensor chip 11 can be discarded as it is. Thus, since the surplus blood 3*a* is also held inside the sensor chip 11 along with the blood 3 that has been introduced into the sensor chip 11 for use in measurement, the surplus blood 3*a* can also be easily disposed of.

Also, the surplus blood inlets 25*a* are provided on both sides (a plurality), namely, the long sides 16*c* and 16*d*, of the sensor chip 11, so the surplus blood 3*a* can be introduced from either long side of the sensor chip 11.

Furthermore, these surplus blood inlets 25*a* are formed in a layer of the sensor chip 11 disposed in the very middle of the three layers that make up the substrate 15. Consequently, even if the user touches the base plate 12 or the cover 14 on the uppermost and lowermost faces of the sensor chip 11, once the surplus blood 3*a* has been taken in it will not adhere to or soil the fingers, etc., or wet the outside.

Also, the inner faces of the surplus blood reservoirs 25 are either given a hydrophilic treatment or formed from a hydrophilic material. The area around the surplus blood reservoirs 25 is also given a hydrophilic treatment or formed from a hydrophilic material. The surplus blood reservoirs 25 also have a large enough volume to hold the surplus blood 3*a*. This prevents the surplus blood 3*a* that has been taken in by capillary action from oozing out from the side faces of the sensor chip 11. Therefore, a used sensor chip 11 that contains surplus blood 3*a* does not have to be wrapped in a tissue 8*a* or the like, and can be disposed of as it is.

Figure 4:
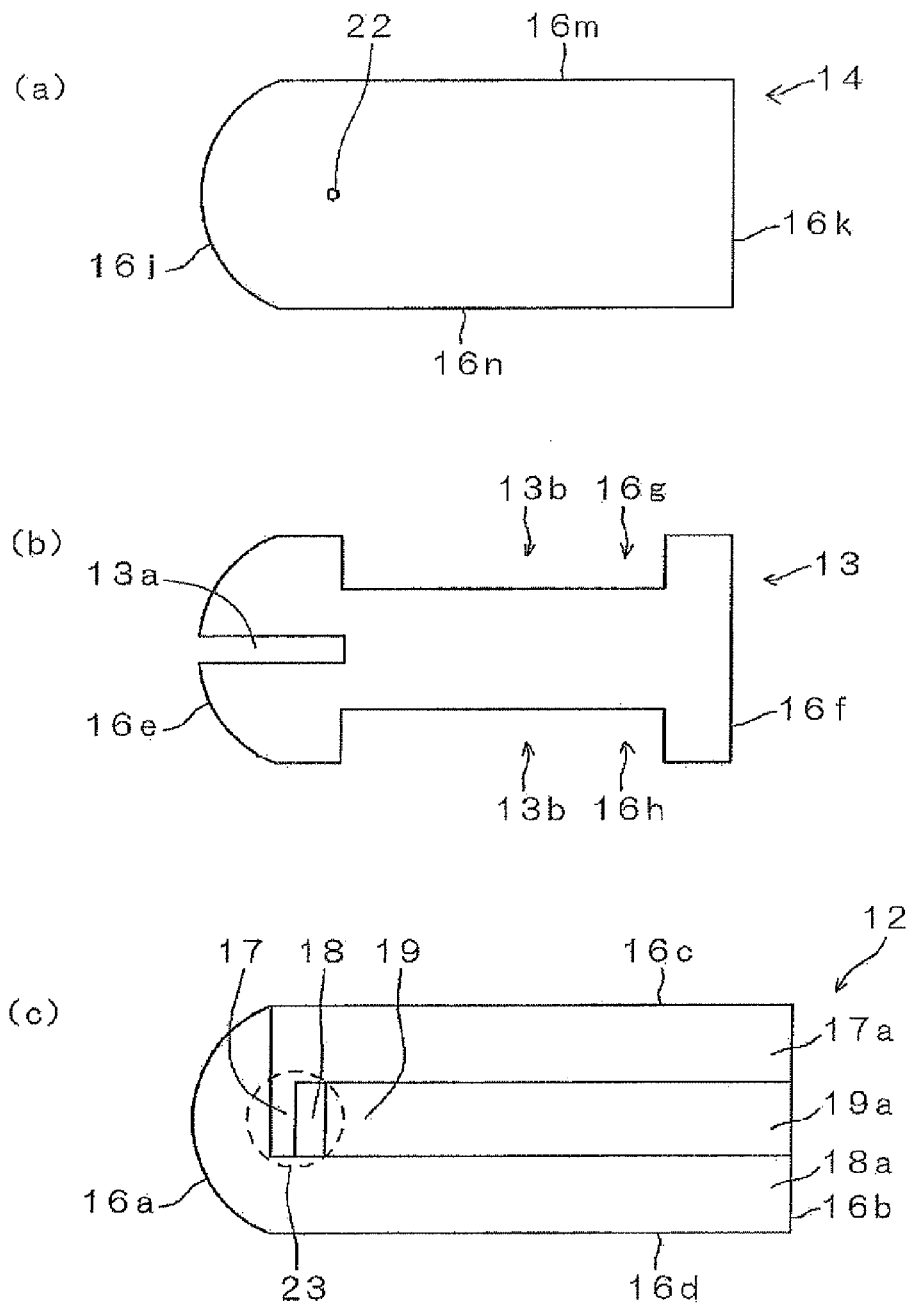
FIG. 4 consists of exploded plan views of the sensor chip in FIG. 1, with FIG. 4a being a plan view of the cover, FIG. 4b a plan view of the spacer, and FIG. 4c a plan view of the base plate.

FIGS. 4*a* to 4*c* are exploded plan views of the sensor chip 11. FIG. 4*c* is a plan view of the base plate 12 of the sensor chip 11. The sensor chip 11 is substantially rectangular in shape (although the short side 16*a* may be semicircular), and the length of its short side 16*a* (on the left in FIG. 4*c*) and its short side 16*b* (on the right in FIG. 4*c*) is approximately 6 mm, while the length of its long sides 16*c* and 16*d* is approximately 20 mm.

The material of the base plate 12 is polyethylene terephthalate (PET) or another such resin-based material. The base plate 12 has a thickness of 0.188 mm (between 0.075 and 0.250 mm) A conductive layer is formed on the upper face of the base plate 12 by sputtering or vapor deposition. This conductive layer is then worked with a laser to integrally form the detection electrodes 17 to 19 and the connection terminals 17*a* to 19*a* that lead out from these detection electrodes 17 to 19.

FIG. 4*b* is a plan view of the spacer 13 of the sensor chip 11. The spacer 13 is substantially rectangular in shape (although the short side 16*e* may be semicircular), and the length of its short sides 16*e* and 16*f* is approximately 6 mm, while the length of its long sides 16*g* and 16*h* is approximately 15 mm. Therefore, when this spacer 13 is affixed over the base plate 12, the connection terminals 17*a* to 19*a* are exposed in a width of approximately 5 mm on the surface.

A slit 13*a* that is 0.6 mm wide and 2.4 mm long is formed from the distal end of the short side 16*e* of the spacer 13 toward the short side 16*f*. The slit 13*a* forms the supply path 21 of the sensor chip 11. The volume of the supply path 21 is 0.14 μL, and a blood glucose value can be measured with just a small amount of blood. Therefore, since a lot of blood is not required to measure a blood glucose value, there is less of a burden on the patient.

Rectangular cut-outs 13*b* are provided on both long sides 16*g* and 16*h* (the upper and lower sides in FIG. 4*b*) of the spacer 13. When the base plate 12 and the cover 14 (discussed below) are laminated, this forms the surplus blood reservoirs 25 (see FIG. 1) in a rectangular shape on both sides of the sensor chip 11, that is, at positions that are in left and right symmetry around the center line of the substrate 15 in its lengthwise direction. The spacer 13 is made of polyethylene terephthalate, and its thickness is 0.100 mm (from 0.050 to 0.125 mm).

FIG. 4*a* is a plan view of the cover 14 of the sensor chip 11. The cover 14 is substantially rectangular in shape (although the short side 16*j* may be semicircular), and the length of its short sides 16*j* and 16*k* (on the left and right in FIG. 4*a*) is approximately 6 mm, while the length of its long sides 16*m* and 16*n* (on the top and bottom in FIG. 4*a*) is approximately 15 mm. Therefore, when this cover 14 is affixed over the spacer 13, the connection terminals 17*a* to 19*a* are exposed in a width of approximately 5 mm on the surface on the short side 16*k*.

The cover 14 has the air hole 22, with a diameter of 0.05 mm, at a location corresponding to the end portion of the slit 13a formed in the spacer 13. The cover 14 is made of polyethylene terephthalate, and its thickness is 0.075 mm (from 0.050 to 0.125 mm).

It is preferable if at least the rear face of the cover 14 corresponding to the ceiling parts of the surplus blood reservoirs 25 and the supply path 21 is given a hydrophilic treatment. This is so the blood 3 will flow more smoothly to the detector 23 under capillary action. Also, the surplus blood 3a will flow more smoothly to the surplus blood reservoirs 25.

If a transparent member is used to form the cover 14, this allows a visual confirmation of how the surplus blood 3a is flowing into the surplus blood reservoirs 25. Furthermore, whether or not the sensor chip 11 has already been used can be easily confirmed from whether or not there is surplus blood 3a in the surplus blood reservoirs 25.

Figure 5:
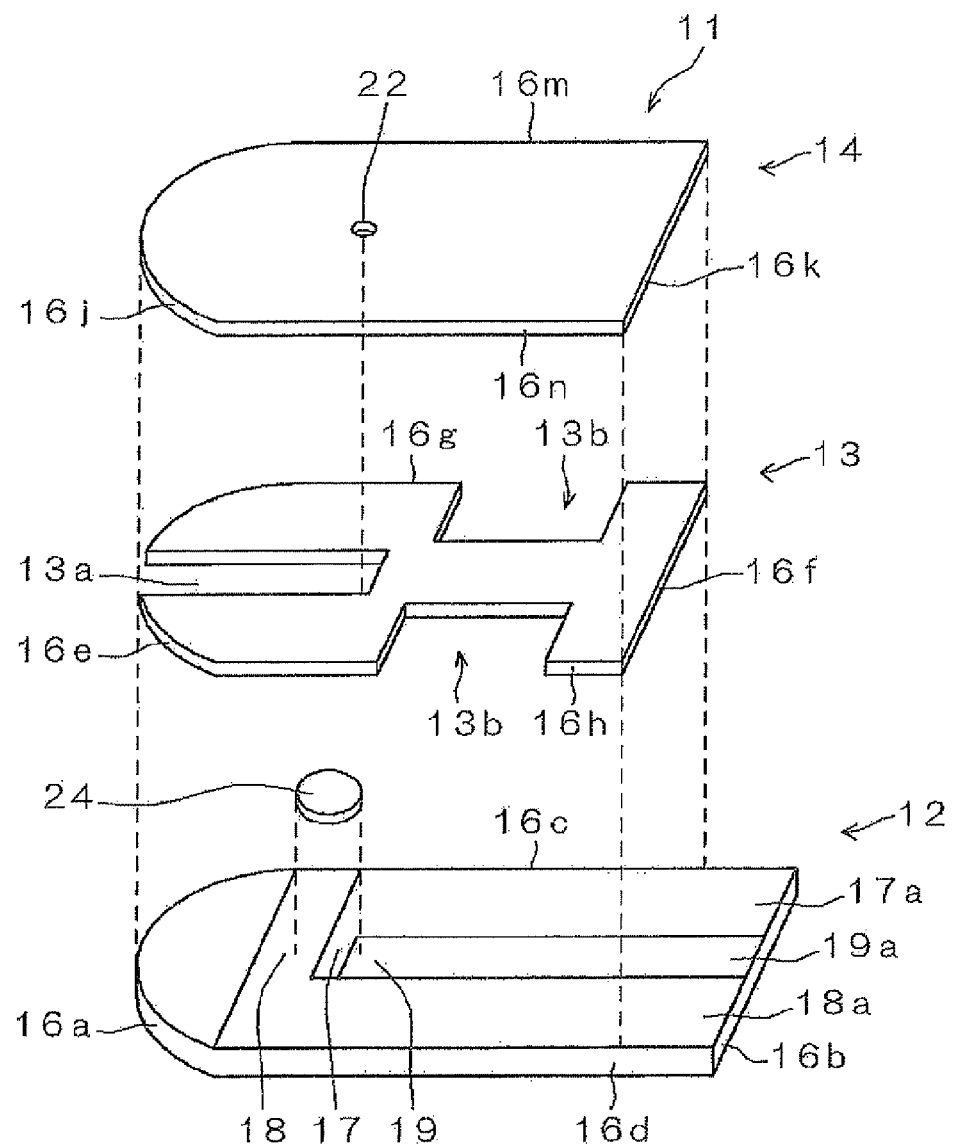
FIG. 5 is an exploded oblique view of the sensor chip in FIG. 1.

FIG. 5 is an exploded oblique view of the above-mentioned sensor chip 11.

The substrate 15 of the sensor chip 11 is constituted by the base plate 12, the spacer 13, and the cover 14. The supply path 21 (see FIG. 1 or 6) is formed by the slit 13a in the spacer 13. The surplus blood reservoirs 25 are formed by the cut-outs 13b in the spacer 13.

Figure 6:
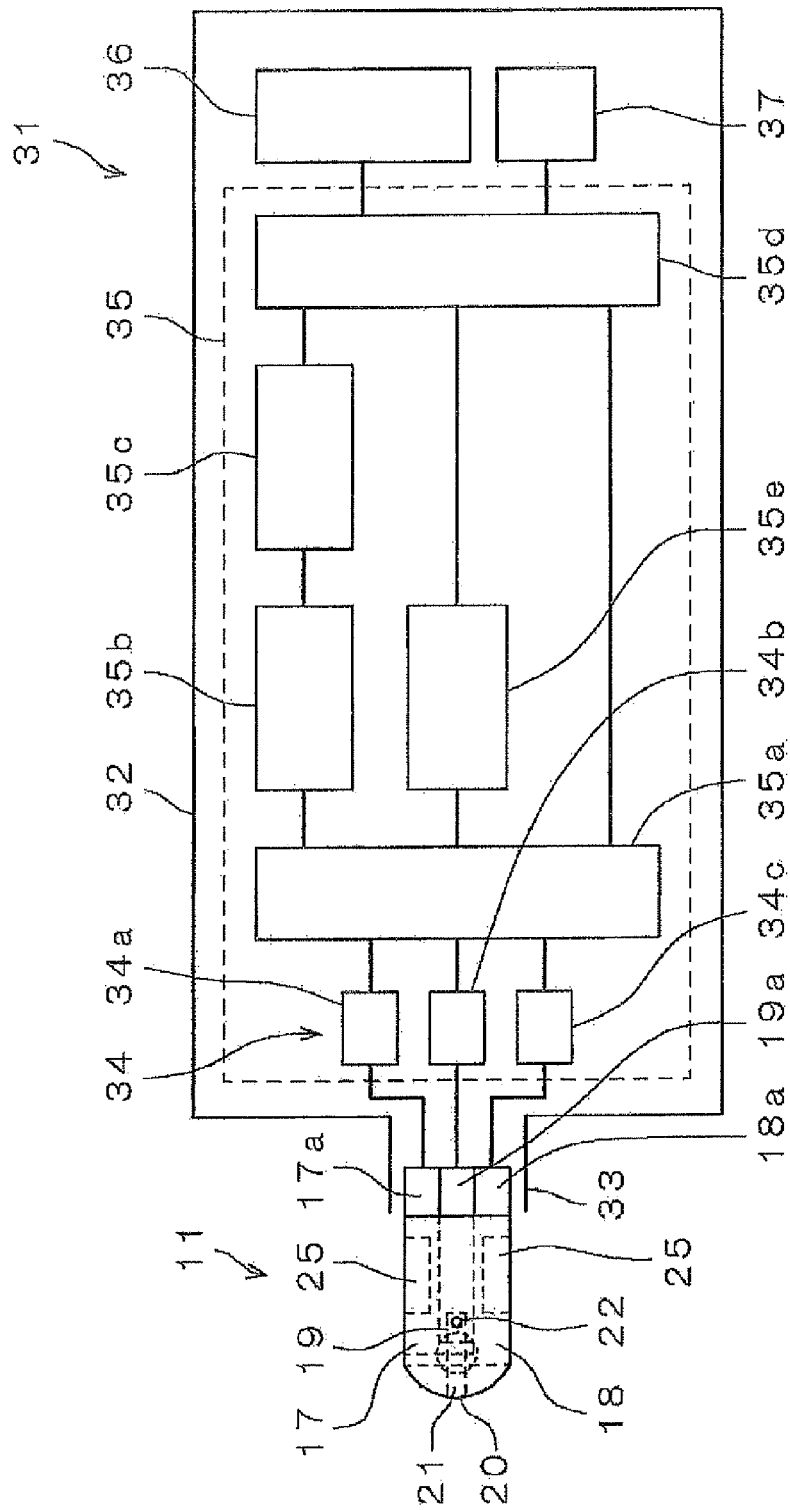
FIG. 6 is a block diagram of a measurement device that makes use of the sensor chip in FIG. 1.

FIG. 6 is a block diagram of the configuration of a measurement device 31 to which the sensor chip 11 is mounted and which measures blood glucose. In FIG. 6, a sensor insertion portion 33 into which the sensor chip 11 is inserted is provided at one end of a housing 32.

A connector 34 (consisting of individual connectors 34a to 34c), to which are connected the connection terminals 17a to 19a formed on the sensor chip 11, is mounted to the inside of the sensor insertion portion 33. The sensor insertion portion 33 allows the insertion of the sensor chips described in embodiments below (except for the sensor chips 111 and 141).

In FIG. 6, 34a is the connector to which the connection terminal 17a is connected, 34b is the connector to which the connection terminal 17b is connected, and 34c is the connector to which the connection terminal 17c is connected.

The connectors 34a, 34b, and 34c are connected to a switching circuit 35a, and are switched according to the measurement details and so forth. The connector 34a is connected to the connection terminal 17a, and is inputted through the switching circuit 35a to a current/voltage converter 35b. The output thereof is connected through an analog/digital converter (hereinafter referred to as an A/D converter) 35c to a computer 35d. The output of the computer 35d is connected to a display component 36 consisting of a liquid crystal or organic EL display.

The computer 35d not only inputs the output of the analog/digital converter 35c, but has the function of controlling the entire measurement device 31. The computer 35d is connected to a communication section 37 that allows the display component 36, the switching circuit 35a, and the control terminal of a reference voltage power supply 35e that applies voltage to the sensor chip 11 to communicate with the outside.

The operation of the measurement device 31 thus configured will be described through reference to FIGS. 6 and 7.

Figure 7:
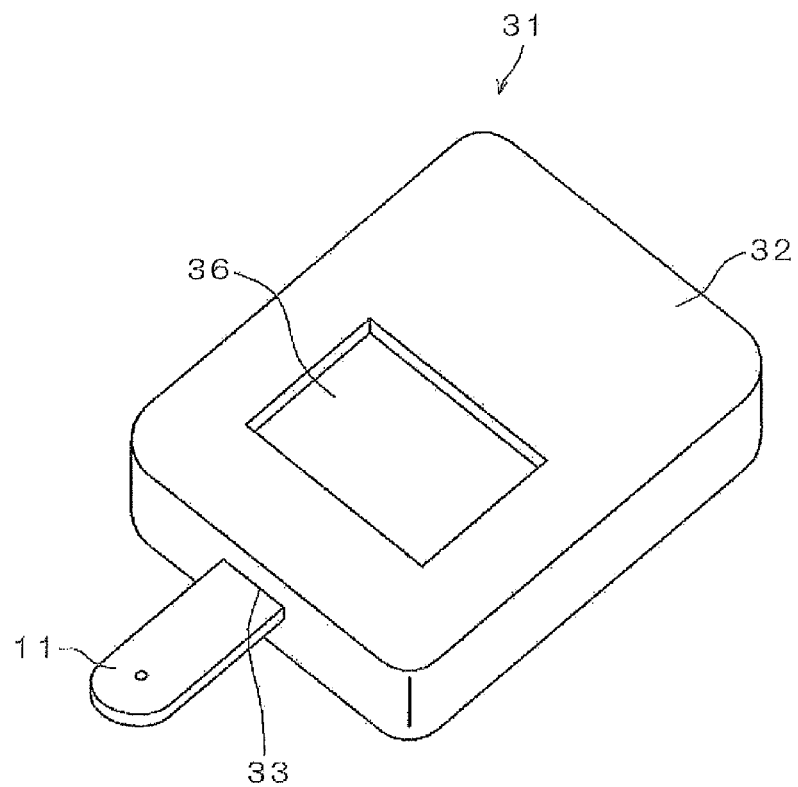
FIG. 7 is an oblique view of when the sensor chip in FIG. 1 has been mounted to a measurement device.

FIG. 7 is an oblique view of when the sensor chip 11 has been inserted into the sensor insertion portion 33 of the measurement device 31.

First, the sensor chip 11 is inserted into the sensor insertion portion 33 of the measurement device 31. Whether or not the sensor chip 11 is in an inserted state can be detected from the change in resistance between the connector 34b and the connector 34c. Specifically, if the sensor chip 11 has not been inserted, the circuit is open between the connector 34b and the connector 34c, so resistance is usually infinitely high. On the other hand, if the sensor chip 11 has been inserted, a specific resistance value will be indicated. This makes it easy to detect that the sensor chip 11 has been inserted into the sensor insertion portion 33. When the sensor chip 11 is inserted into the sensor insertion portion 33 of the measurement device 31, the connection terminals 17a, 19a, and 18a are respectively connected to the connectors 34a, 34b, and 34c of a measurement circuit 35.

Next, in a state in which the sensor chip 11 has been mounted to the sensor insertion portion 33 (see FIG. 7), if a drop of measurement-use blood 3 is applied to the inlet 20 of the sensor chip 11, the blood 3 is guided by capillary action through the supply path 21, which communicates with the inlet 20, onto a detection electrode 19 disposed the farthest downstream. From the fact that the blood 3 has been introduced onto the detection electrode 19, it can be detected that the blood 3 has sufficiently reached the detection electrode 17 and the detection electrode 18.

The computer 35d controls the switching circuit 35a so that the detection electrode 18 is connected to ground. For a specific length of time after this, no voltage is supplied from the current/voltage converter 35b to the detection electrode 17. During this time, a reaction proceeds between the blood 3 and a reagent 24 placed on the detection electrode 17 and the detection electrode 18. Once a specific length of time (2 to 5 seconds) has elapsed, the reference voltage power supply 35e applies a specific voltage between the detection electrode 17 and the detection electrode 18 of the sensor chip 11 via the switching circuit 35a and the connector 34. At this point, current that is proportional to the blood glucose concentration in the blood 3 is produced between the detection electrode 17 and the detection electrode 18.

This current goes through the connector 34 and the switching circuit 35a, is inputted to the current/voltage converter 35b, and is converted into voltage. This voltage is converted into digital data by the A/D converter 35c. The converted digital data is taken in by the computer 35d. The computer 35d computes a blood glucose value from the digital data, and displays it on the display component 36.

Embodiment 2

Next, a sensor chip 41 in Embodiment 2 (corresponds to the sensor chip 11 in Embodiment 1) will be described through reference to FIGS. 8 to 11.

The sensor chip 41 in Embodiment 2 differs from Embodiment 1 above in that surplus blood reservoirs 42 (correspond to the surplus blood reservoirs 25 in Embodiment 1) are formed in a different layer from that of the supply path 21. Furthermore, in Embodiment 2 here, those components that are the same as in Embodiment 1 will be numbered the same and will not be described again. The same applies to all subsequent embodiments.

Figure 8:
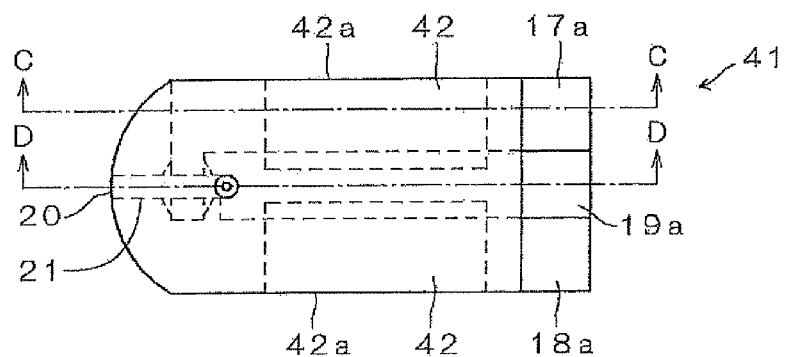
FIG. 8 is a plan view of the sensor chip pertaining to Embodiment 2 of the present invention.
Figure 9:
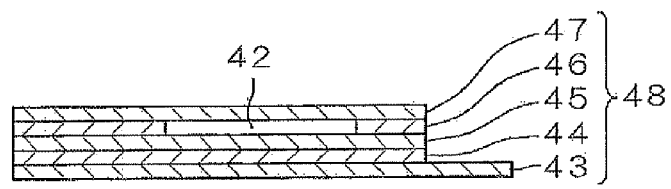
FIG. 9 is a C-C cross section of FIG. 8.
Figure 10:
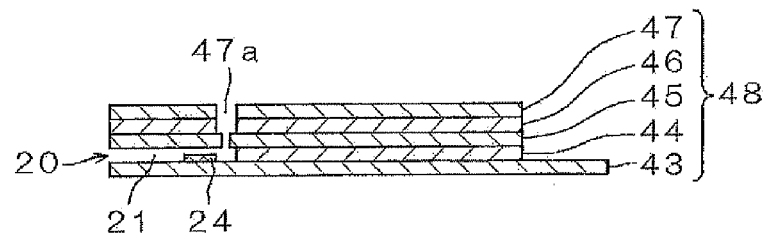
FIG. 10 is a D-D cross section of FIG. 8.
Figure 11:
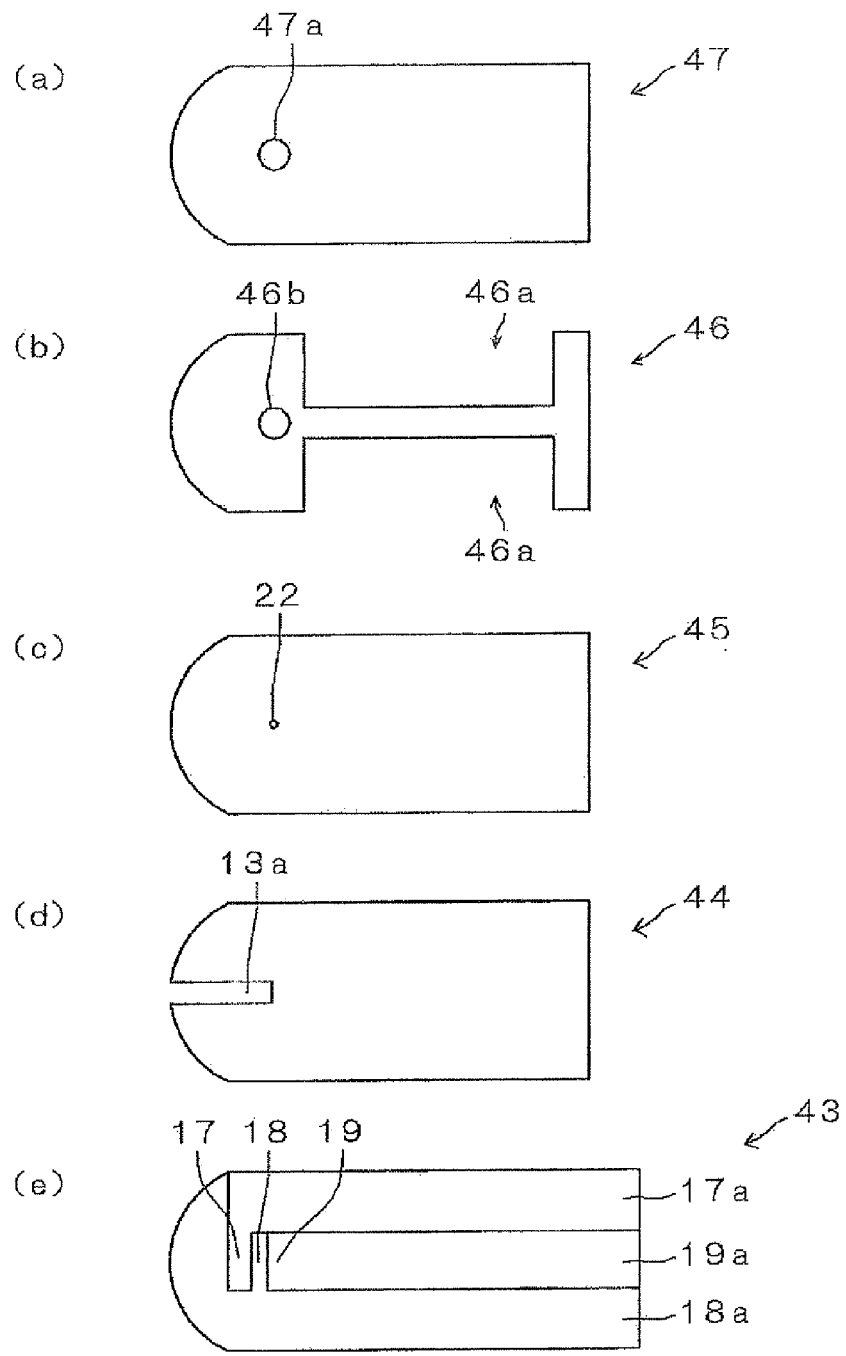
FIG. 11 consists of exploded plan views of FIG. 8, with FIG. 11a being a plan view of a cover used for surplus blood suction, FIG. 11b a plan view of a spacer used for surplus blood suction, FIG. 11c a plan view of the cover, FIG. 11d a plan view of the spacer, and FIG. 11e a plan view of the base plate.

FIG. 8 is a plan view of the sensor chip 41 pertaining to Embodiment 2, FIG. 9 is a C-C cross section of FIG. 8, and FIG. 10 is a D-D cross section of FIG. 8.

As shown in FIGS. 9 and 10, the sensor chip 41 has a five-layer structure that includes a base plate 43 (corresponds to the base plate 12 in Embodiment 1), a spacer 44 that is affixed to the top face of the base plate 43 (corresponds to the spacer 13 in Embodiment 1), a cover 45 that is affixed to the top face of the spacer 44 (corresponds to the cover 14 in Embodiment 1), a surplus blood suction-use spacer 46 that is affixed to the top face of the cover 45, and a surplus blood suction-use cover 47 that is affixed to the top face of the surplus blood suction-use spacer 46.

The base plate 43, the spacer 44, the cover 45, the surplus blood suction-use spacer 46, and the surplus blood suction-use cover 47 form a substrate 48 in the form of a flat board.

Except for its thickness, the sensor chip 41 has the same external shape as the sensor chip 11 in Embodiment 1, and the same material is used for each. The external shape and material of the surplus blood suction-use spacer 46 are the same as those of the spacer 13 in Embodiment 1, and the external shape and material of the surplus blood suction-use cover 47 are the same as those of the cover 14 in Embodiment 1.

FIGS. 11a to 11e are exploded plan views of the sensor chip 41.

FIG. 11e is a plan view of the base plate 43 of the sensor chip 41, which has the same configuration as the base plate 12 of the sensor chip 11 in Embodiment 1 above.

FIG. 11d is a plan view of the spacer 44 of the sensor chip 41, which is provided with a slit 13a that forms a supply path 21 (see FIG. 8 or 10).

The spacer 44 differs from the spacer 13 in Embodiment 1 above in that it is not provided with the rectangular cut-outs 13b that form the surplus blood reservoirs 25.

FIG. 11c is a plan view of the cover 45 of the sensor chip 41, which has the same configuration as the cover 14 in Embodiment 1 above. It is not necessary to use a transparent member for the material of this cover 45.

FIG. 11b is a plan view of the surplus blood suction-use spacer 46 of the sensor chip 41. The surplus blood suction-use spacer 46 has rectangular cut-outs 46a that form surplus blood reservoirs 42 (see FIGS. 8 and 9), which are formed on both long sides at locations that are symmetrical around the center line of the substrate 48 in the lengthwise direction. The surplus blood suction-use spacer 46 also has a through-hole 46b that is larger in diameter than the air hole 22 of the cover 45, at a location corresponding to the air hole 22.

FIG. 11a is a plan view of the surplus blood suction-use cover 47 of the sensor chip 41. The surplus blood suction-use cover 47 has a through-hole 47a formed at a location corresponding to the through-hole 46b in the surplus blood suction-use spacer 46. This surplus blood suction-use cover 47 is preferably formed using a transparent member. The reason is the same as in Embodiment 1.

With the sensor chip 41 in Embodiment 2, the volume of the surplus blood reservoirs 42 can be larger than that in the sensor chip 11 in Embodiment 1 above. More specifically, a volume of about two-thirds the volume of the substrate 48 of the sensor chip 41 can be ensured, at most. Everything else is the same as with the sensor chip 11 in Embodiment 1.

Because of the above, when the sensor chip 41 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiment can be obtained, e.g., surplus blood can be easily dealt with, and work efficiency can be improved.

Embodiment 3

Figure 16:
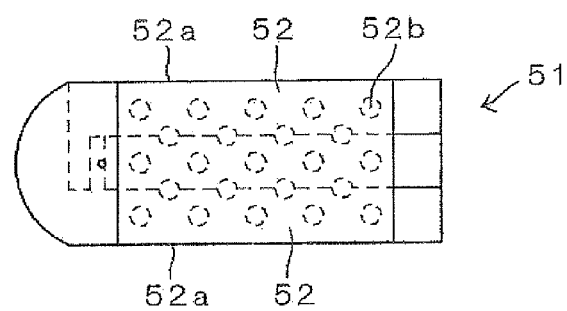
FIG. 16 is a plan view of the sensor chip in FIG. 12.

As shown in FIG. 16, the sensor chip 51 in Embodiment 3 (corresponds to the sensor chip 41 in Embodiment 2) differs from the sensor chip 41 in Embodiment 2 above only in the configuration of its surplus blood reservoirs 52. Specifically, in Embodiment 3, a plurality of bumps 52b are provided inside the surplus blood reservoirs 52 in order to increase the thickness strength of the surplus blood reservoirs 52. Consequently, even when pressure is applied to the sensor chip 51 in the thickness direction, the thickness dimension can be kept substantially constant. Also, even if a pressing force is applied from the outside in the thickness direction of the surplus blood reservoirs 52, there is almost no bending of the sensor chip 51 in the thickness direction due to the pressing force, so the surplus blood 3a can be prevented from flowing out of surplus blood inlets 52a.

Figure 12:
FIG. 12 consists of exploded plan views showing the configuration of surplus blood reservoirs provided to the sensor chip pertaining to Embodiment 3 of the present invention, with FIG. 12a being a plan view of a cover used for surplus blood suction, and FIG. 12b a plan view of a spacer used for surplus blood suction.
Figure 12:
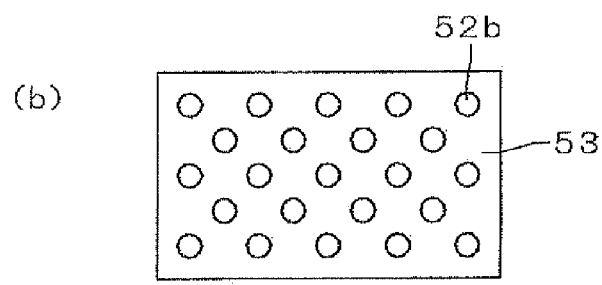

In Embodiment 3, as shown in FIG. 12b, the bumps 52b are disposed on the top face of a rectangular surplus blood suction-use spacer 53 in order to form the surplus blood reservoirs 52. The height of these bumps 52b is approximately 0.1 mm (from 0.050 to 0.125 mm). Specifically, this is the same as the spacer 13 in Embodiment 1 in that capillary action is produced by a tiny gap defined by this height.

The plurality of bumps 52b are formed uniformly within the surplus blood reservoirs 52. For example, the fewer bumps 52b there are, essentially the greater is the volume of the surplus blood reservoirs 52. On the other hand, the more bumps 52b there are, the volume of the surplus blood reservoirs 52 essentially decreases, but the strength increases in the thickness direction of the surplus blood reservoirs 52. In view of this, in this embodiment 23 of the bumps 52b are provided so as to strike a good balance between these factors. The number of bumps 52b may be suitably increased or decreased according to the surface area of the surplus blood reservoirs of the sensor chip 51.

Again in Embodiment 3, just as in Embodiment 2 above, the volume of the surplus blood reservoirs 52 can be increased, and can be expanded to about two-thirds the volume of the substrate of the sensor chip 51.

As shown in FIG. 12a, a surplus blood suction-use cover 54 is affixed to the top face of the surplus blood suction-use spacer 53.

Figure 13:
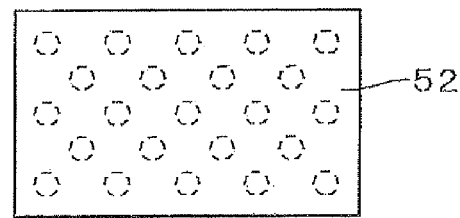
FIG. 13 is a plan view of the surplus blood reservoirs of the sensor chip in FIG. 12.

The surplus blood suction-use cover 54 is same size as the surplus blood suction-use spacer 53. FIG. 13 is a plan view of the surplus blood reservoirs 52 formed by affixing the surplus blood suction-use spacer 53 together with the surplus blood suction-use cover 54.

Figure 14:
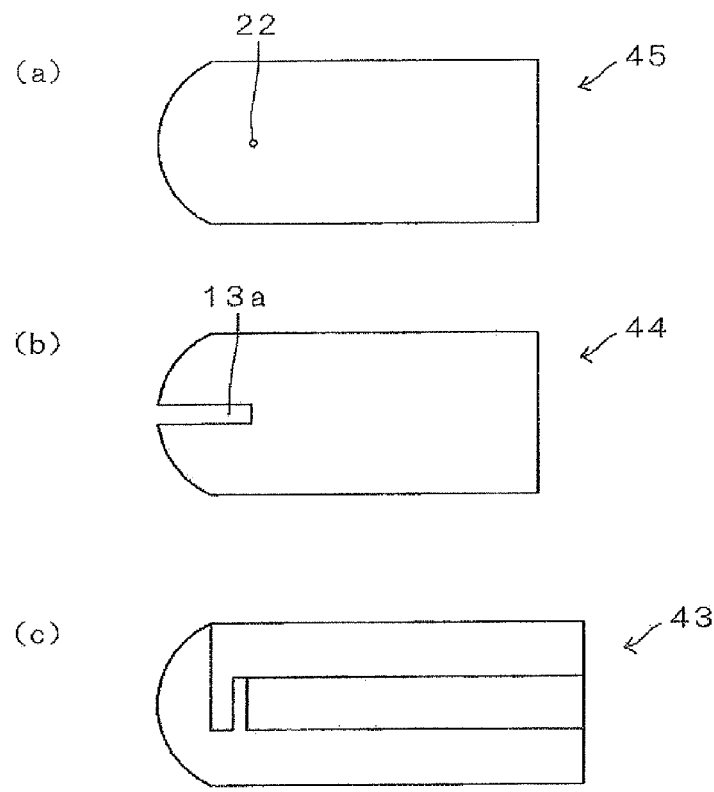
FIG. 14 consists of exploded plan views of the blood measurement portion of the sensor chip in FIG. 12, with FIG. 14a being a plan view of a cover, FIG. 14b a plan view of a spacer, and FIG. 14c a plan view of a base plate.
Figure 15:
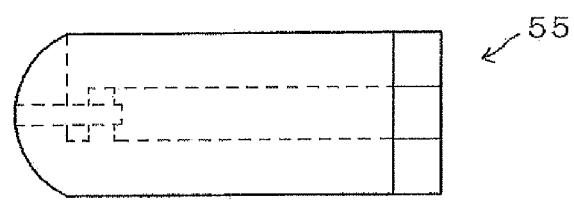
FIG. 15 is a plan view of the blood measurement portion constituting the sensor chip in FIG. 12.

FIG. 15 is a plan view of a blood measurement portion 55. The blood measurement portion 55 is made up of the base plate 43 (see FIG. 14c), the spacer 44 affixed to the top face of the base plate 43 (see FIG. 14b), and the cover 45 affixed to the top face of the spacer 44 (see FIG. 14a). The surplus blood reservoirs 52 shown in FIG. 13 are affixed to the top face of the blood measurement portion 55 to complete the sensor chip 51 shown in FIG. 16.

The bumps 52b of the surplus blood reservoirs 52 here may be dots that are coated with glue and affixed to the rear face of the surplus blood suction-use cover 54. A hot-melt material can also be used for the glue. Consequently, there is no need for the surplus blood suction-use spacer 53 as a separate member, so fewer parts are required and the cost can be lowered.

The bumps 52b may also be produced by subjecting the surplus blood suction-use cover 54 to embossing that protrudes toward the rear face.

Because of the above, when the sensor chip 51 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 4

Figure 18:
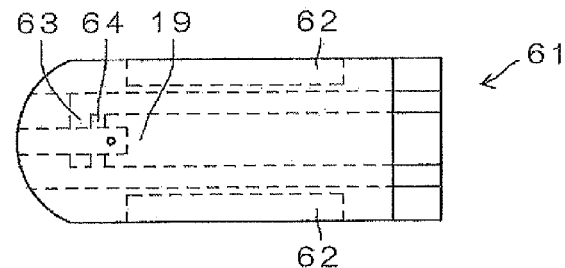
FIG. 18 is a plan view of the sensor chip in FIG. 17.

FIG. 18 is a plan view of a sensor chip 61 in Embodiment 4 (corresponds to the sensor chip 11 in Embodiment 1).

The sensor chip 61 in this embodiment differs from Embodiment 1 above in that surplus blood reservoirs 62 do not come into contact with a detection electrode 63 (corresponds to the detection electrode 17 in Embodiment 1) or a detection electrode 64 (corresponds to the detection electrode 18 in Embodiment 1). With this configuration, the surplus blood reservoirs 62 does not affect the detection electrodes 63 and 64.

Figure 17:
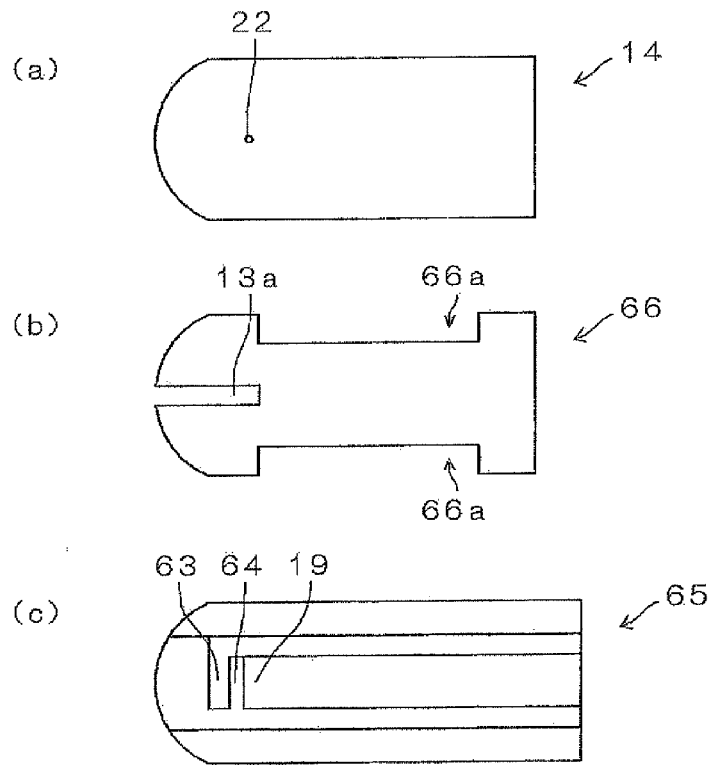
FIG. 17 consists of exploded plan views of the sensor chip pertaining to Embodiment 4 of the present invention, with FIG. 17a being a plan view of a cover, FIG. 17b a plan view of a spacer, and FIG. 17c a plan view of a base plate.

FIGS. 17a to 17c are exploded plan views of the sensor chip 61. FIG. 17c is a plan view of a base plate 65 (corresponds to the base plate 12 in Embodiment 1). In this embodiment, the width of the detection electrodes 63 and 64 is narrower than the width of the detection electrodes 17 and 18 of the s base plate 12 in the sensor chip 11 of Embodiment 1 above. FIG. 17b is a plan view of a spacer 66 (corresponds to the spacer 13 in Embodiment 1). Cut-outs 66a that form the surplus blood reservoirs 62 are narrow enough that they do not come into contact with the detection electrodes 63 and 64. FIG. 17a is a cover 14 affixed to the top face of the spacer 66.

With this embodiment, the sensor chip 61 is constituted by combining these members (the base plate 65, the spacer 66, and the cover 14).

Because of the above, when the sensor chip 61 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 5

Figure 20:
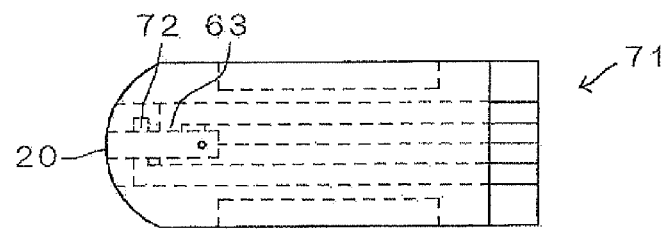
FIG. 20 is a plan view of the sensor chip in FIG. 19.

FIG. 20 is a plan view of a sensor chip 71 in Embodiment 5 (corresponds to the sensor chip 61 in Embodiment 4).

The sensor chip 71 in this embodiment differs from Embodiment 4 above in that a detection electrode 72 (Hct electrode) is provided between the inlet 20 and the detection electrode 63. This difference makes it possible to correct the measured value in a blood test, which improves measurement accuracy.

Figure 19:
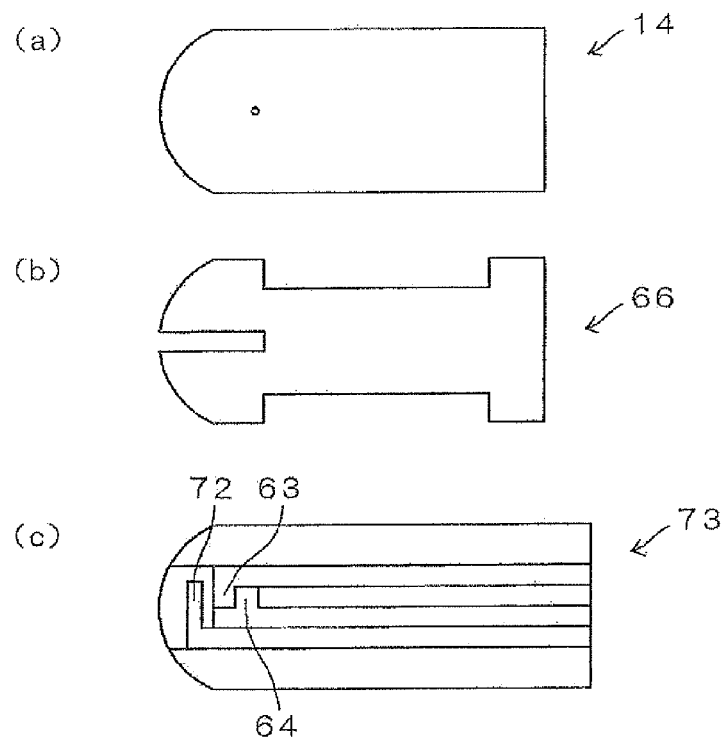
FIG. 19 consists of exploded plan views of the sensor chip pertaining to Embodiment 5 of the present invention, with FIG. 19a being a plan view of a cover, FIG. 19b a plan view of a spacer, and FIG. 19c a plan view of a base plate.

FIGS. 19a to 19c are exploded plan views of the sensor chip 71 in FIG. 20. FIG. 19c is a plan view of a base plate 73 (corresponds to the base plate 65 in Embodiment 4). The base plate 73 is provided with the detection electrode 72 between the detection electrode 63 and the inlet 20. FIG. 19b is a plan view of the spacer 66. The spacer 66 is affixed to the top face of the base plate 73. FIG. 19a is a plan view of the cover 14 affixed to the top face of the spacer 66.

With this embodiment, the sensor chip 71 is constituted by combining these members (the base plate 73, the spacer 66, and the cover 14).

Because of the above, when the sensor chip 71 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 6

Figure 22:
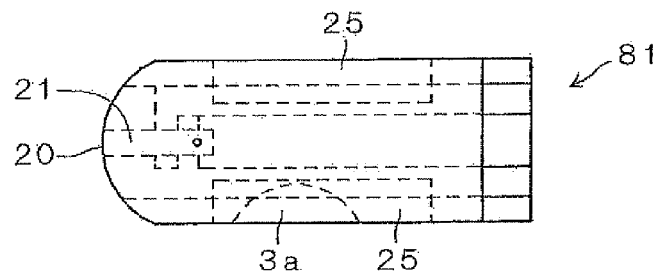
FIG. 22 is a plan view of the sensor chip in FIG. 21.

FIG. 22 is a plan view of a sensor chip 81 in Embodiment 6 (corresponds to the sensor chip 11 in Embodiment 1).

The sensor chip 81 in this embodiment differs from Embodiment 1 above in that the flow of the blood 3 into the surplus blood reservoirs 25 can be detected electrically.

Consequently, even if the blood 3 should be accidentally introduced into the surplus blood reservoirs 25, a notice to this effect can be displayed on the display component 36 of the measurement device 31 (see FIG. 6) to notify the patient.

Figure 21:
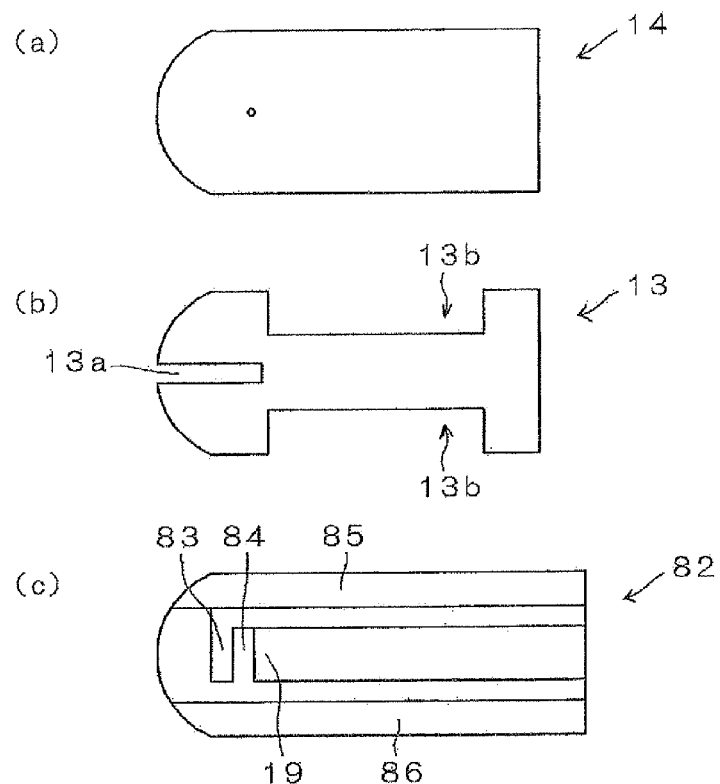
FIG. 21 consists of exploded plan views of the sensor chip pertaining to Embodiment 6 of the present invention, with FIG. 21a being a plan view of a cover, FIG. 21b a plan view of a spacer, and FIG. 21c a plan view of a base plate.

FIGS. 21a to 21c are exploded plan views of the sensor chip 81.

FIG. 21c is a plan view of a base plate 82 (corresponds to the base plate 12 in Embodiment 1). With the base plate 82, the portion corresponding to the detection electrode 17 of the sensor chip 11 in Embodiment 1 above (see FIG. 4c) is divided in two lengthwise to form a detection electrode 83 (working electrode) and a surplus blood detection electrode 85. The portion corresponding to the detection electrode 18 of the sensor chip 11 in Embodiment 1 above (see FIG. 4c) is divided in two lengthwise to form a detection electrode 84 (counter electrode) and a surplus blood detection electrode 86.

FIG. 21b is a plan view of the spacer 13. The spacer 13 is affixed to the top face of the base plate 82. Cut-outs 13b formed in the spacer 13 are provided at positions that are in left and right symmetry around the center line of the base plate 82 in its lengthwise direction. The cut-outs 13b have a dimensional relation such that they straddle the detection electrode 83, the surplus blood detection electrode 85, the detection electrode 84, and the surplus blood detection electrode 86. This is because the flow of the blood 3 into the surplus blood reservoirs 25 is electrically detected. Also, the slit 13a and the cut-outs 13b are provided at locations that are separated from each other. Specifically, the supply path 21 and the surplus blood reservoirs 25 are disposed at mutually independent locations, and the blood 3 and the surplus blood 3a that flow into them and are held there do not affect each other.

FIG. 21a is the cover 14 affixed to the top face of the spacer 13.

Since the sensor chip 81 in this embodiment is configured as above, the flow of the blood 3 or the surplus blood 3a into the surplus blood reservoirs 25 can be detected by applying voltage between the detection electrode 83 and the surplus blood detection electrode 85, the detection electrode 84, and the surplus blood detection electrode 86 and measuring the electrically between them.

For example, if the flow of the blood 3 into the surplus blood reservoirs 25 is detected before the blood 3 has flowed into the supply path 21, information recommending that the blood 3 be introduced into the supply path 21 is displayed on the display component 36 (see FIG. 6) to notify the user. The flow of the blood 3 into the supply path 21 is detected by applying voltage between the detection electrode 84 and the detection electrode 19 and measuring the electrical resistance.

The surplus blood detection electrodes 85 and 86 in this embodiment can also be applied to the sensor chip 71 having the detection electrode 72 (Hct electrode) given in Embodiment 5 above.

Because of the above, when the sensor chip 81 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 7

Figure 24:
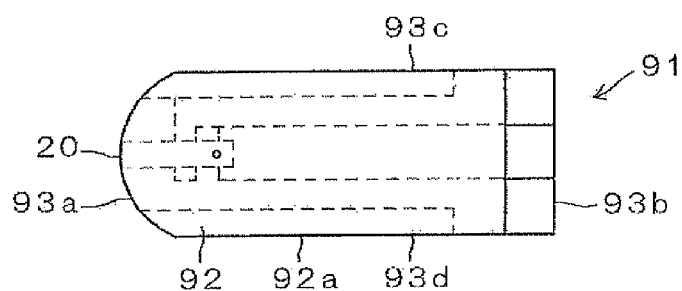
FIG. 24 is a plan view of the sensor chip in FIG. 23.

FIG. 24 is a plan view of a sensor chip 91 in Embodiment 7 (corresponds to the sensor chip 11 in Embodiment 1).

The sensor chip 91 in this embodiment differs from the sensor chip 11 in Embodiment 1 above in that surplus blood inlets 92a that communicate with surplus blood reservoirs 92 are formed at the upper side (on a first end side) of a short side 93a and on a long side 93c of the substantially rectangular sensor chip 91, and at the lower side (on a second end side) of the short side 93a and on a long side 93d. Therefore, after the measurement-use blood 3 has flowed into the inlet 20, the surplus blood 3a can be introduced into the surplus blood reservoirs 92 provided on the short side 93a merely by slightly moving the sensor chip 91.

Figure 23:
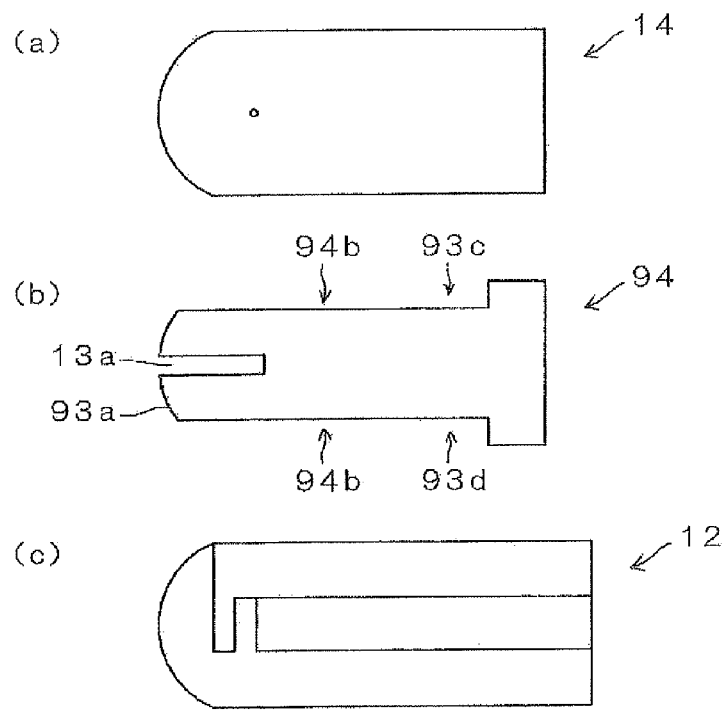
FIG. 23 consists of exploded plan views of the sensor chip pertaining to Embodiment 7 of the present invention, with FIG. 23a being a plan view of a cover, FIG. 23b a plan view of a spacer, and FIG. 23c a plan view of a base plate.

FIGS. 23a to 23c are exploded plan views of the sensor chip 91.

FIG. 23a is a plan view of the base plate 12. The spacer 94 shown in FIG. 23b (corresponds to the spacer 13 in Embodiment 1) is affixed to the top face of the base plate 12.

The spacer 94 is provided with cut-outs 94b at a portion from the upper side of the short side 93a of the substantially rectangular spacer 94 to the long side 93c, and at a portion from the lower side of the short side 93a to the long side 93d. These cut-outs 94b form the surplus blood reservoirs 92 and the surplus blood inlets 92a. Also, the cut-outs 94b are provided at locations that are separate from the slit 13a that forms the inlet 20. The cover 14 shown in FIG. 23a is affixed to the top face of this spacer 94.

In this embodiment, the sensor chip 91 is constituted by combining these members (the base plate 12, the spacer 94, and the cover 14).

Because of the above, when the sensor chip 91 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 8

Figure 26:
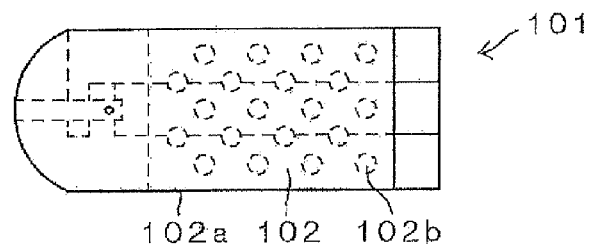
FIG. 26 is a plan view of the sensor chip in FIG. 25.

FIG. 26 is a plan view of a sensor chip 101 in Embodiment 8 (corresponds to the sensor chip 11 in Embodiment 1).

The sensor chip 101 forms a large-scale surplus blood reservoir 102 through the sensor chip 101 in Embodiment 8 has three-layer structure. An increase in strength is achieved by providing a plurality of bumps 102b inside the surplus blood reservoir 102.

Figure 25:
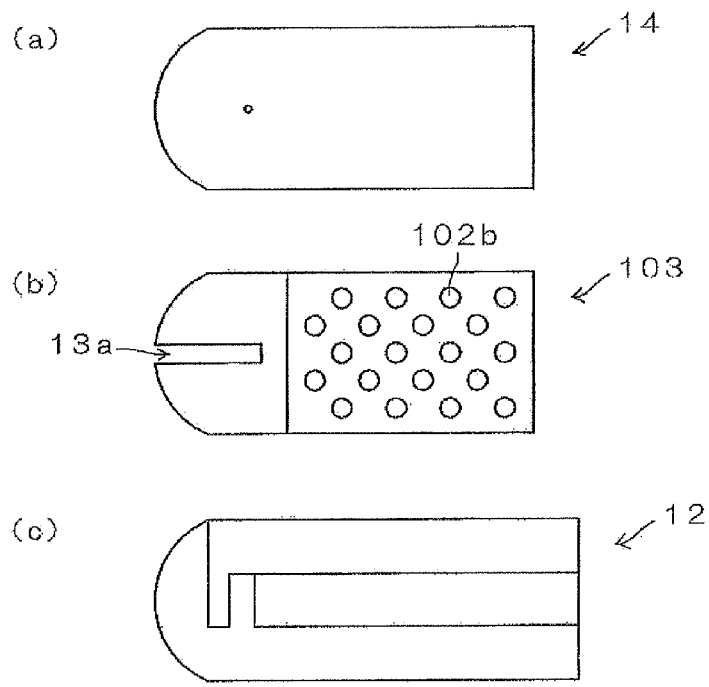
FIG. 25 consists of exploded plan views of the sensor chip pertaining to Embodiment 8 of the present invention, with FIG. 25a being a plan view of a cover, FIG. 25b a plan view of a spacer, and FIG. 25c a plan view of a base plate.

FIGS. 25a to 25c are exploded plan views of the sensor chip 101.

FIG. 25c is a plan view of the base plate 12. The spacer 103 shown in FIG. 25b (corresponds to the spacer 13 in Embodiment 1) is affixed to the top face of the base plate 12.

The spacer 103 has the slit 13a formed in the substantially rectangular spacer 103, and the plurality of bumps 102b formed over the entire interior of this slit 13a. The bumps 102b are formed in the same manner as the bumps 52b in Embodiment 3 above (see FIGS. 12 and 16). The cover 14 shown in FIG. 25a is affixed to the top face of the spacer 103.

With this embodiment, the sensor chip 101 is constituted by combining these members (the base plate 12, the spacer 103, and the cover 14).

Because of the above, when the sensor chip 101 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 9

Figure 28:
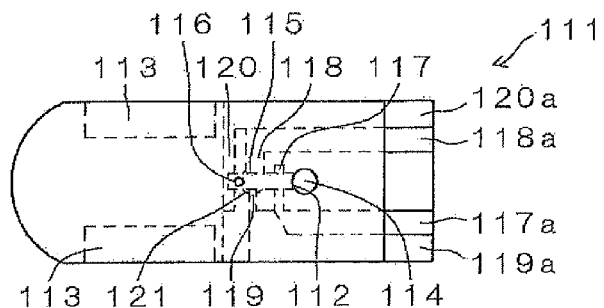
FIG. 28 is a plan view of the sensor chip in FIG. 27.

FIG. 28 is a plan view of a sensor chip 111 in Embodiment 9 (corresponds to the sensor chip 11 in Embodiment 1).

With the sensor chip 111 in this embodiment, surplus blood reservoirs 113 is provided to at least one lateral face of the substantially rectangular sensor chip 111, and an inlet 112 for the blood 3 is provided in the approximate center in plan view. The sensor chip 111 is used in a blood test device (one-step) for measuring the properties of the blood 3 simultaneously with puncture (see FIG. 31).

A reservoir 114 for the blood 3 is formed in the approximate center of the sensor chip 111 in plan view. The reservoir 114 has a circular shape, with a diameter of approximately 2 mm. The inlet 112, into which measurement-use blood 3 flows, is provided on the lateral face of the reservoir 114.

Also, a supply path 115 (corresponds to the supply path 21 in Embodiment 1) is formed communicating with the inlet 112. A air hole 116 is provided to the end of this supply path 115. The various electrodes constituting a detector 121 (a detection electrode 117 (Hct electrode), a detection electrode 118 (counter electrode), a detection electrode 119 (working electrode), and a detection electrode 120) are provided in that order on the supply path 115, from the reservoir 114 direction. The reagent 24 (see FIG. 2) is placed on the detector 121. The detection electrodes 117, 118, 119, and 120 are routed to the end in the lengthwise direction of the sensor chip 111 and connected to connection terminals 117a, 118a, 119a, and 120a.

The surplus blood reservoirs 113 are formed on the lateral face portion of the sensor chip 111.

Figure 27:
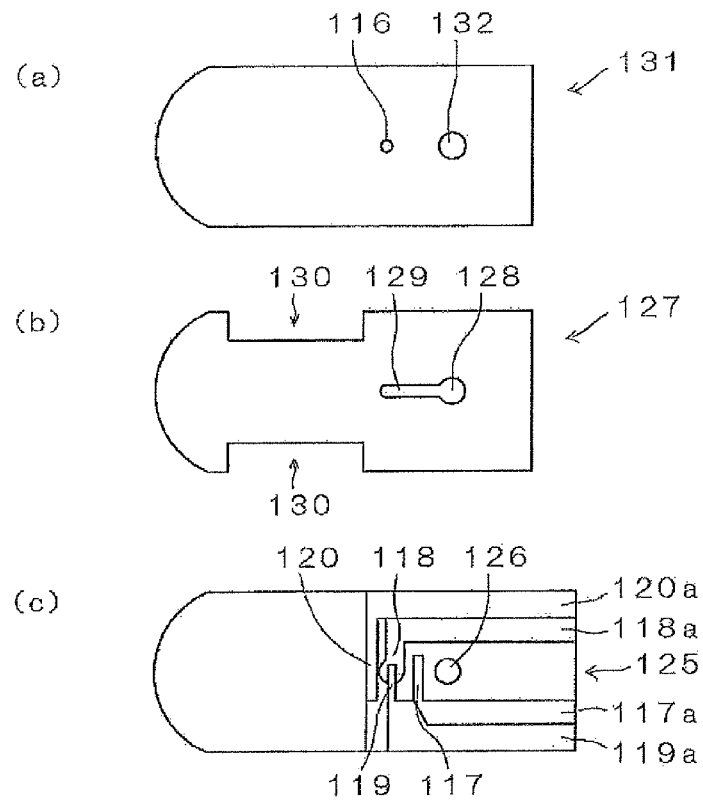
FIG. 27 consists of exploded plan views of the sensor chip pertaining to Embodiment 9 of the present invention, with FIG. 27a being a plan view of a cover, FIG. 27b a plan view of a spacer, and FIG. 27c a plan view of a base plate.

FIGS. 27a to 27c are exploded plan views of the sensor chip 111.

FIG. 27c is a plan view of a substantially rectangular base plate 125 (corresponds to the base plate 12 in Embodiment 1). The base plate 125 is provided with a hole 126 formed at a location corresponding to the reservoir 114, the detection electrodes 117, 118, 119, and 120, and the connection terminals 117a, 118a, 119a, and 120a that lead out from these detection electrodes.

The spacer 127 shown in FIG. 27b (corresponds to the spacer 13 in Embodiment 1) is affixed to the top face of the base plate 125. The spacer 127 is provided with a hole 128 corresponding to the reservoir 114, a slit 129 provided at a location corresponding to the supply path 115 and communicating with this hole 128, and cut-outs 130 at locations corresponding to the surplus blood reservoirs 113.

The cover 131 shown in FIG. 27a is affixed to the top face of the spacer 127. The cover 131 is provided with a hole 132 and an air hole 116 at locations corresponding to the reservoir 114. The reservoir 114 here is constituted by the hole 126 provided to the base plate 125, the hole 128 provided to the spacer 127, and the hole 132 provided to the cover 131.

With this embodiment, the sensor chip 111 is constituted by combining these members (the base plate 125, the spacer 127, and the cover 131).

Because of the above, when the sensor chip 111 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 10

Figure 30:
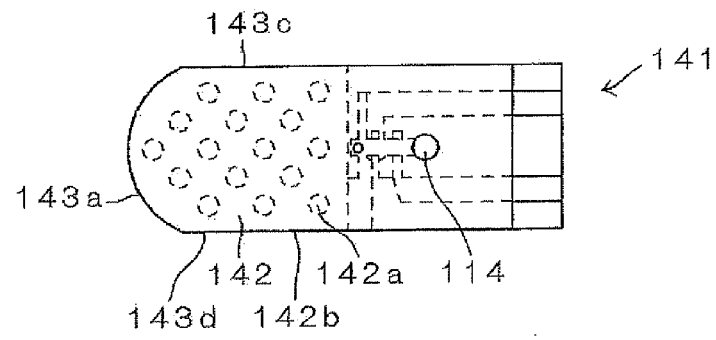
FIG. 30 is a plan view of the sensor chip in FIG. 29.

FIG. 30 is a plan view of a sensor chip 141 in Embodiment 10 (corresponds to the sensor chip 111 in Embodiment 9).

The sensor chip 141 in this embodiment comprises a surplus blood reservoir 142 on one entire lateral face of the substantially rectangular sensor chip 141. A plurality of bumps 142a are provided on the inside of the surplus blood reservoir 142. Therefore, just as in Embodiment 8 above, the strength of the surplus blood reservoir 142 can be increased. A surplus blood inlet 142b of the surplus blood reservoir 142 is provided on a short side 143a of the sensor chip 141 and both long sides 143c and 143d, and can drawn in surplus blood 3a from any of these three directions of the sensor chip 141.

Figure 29:
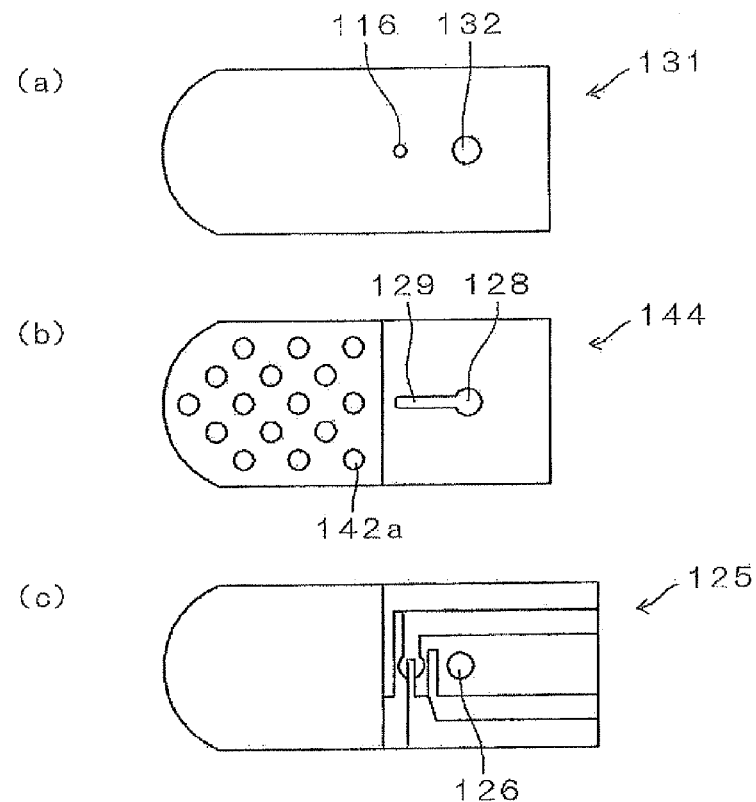
FIG. 29 consists of exploded plan views of the sensor chip pertaining to Embodiment 10 of the present invention, with FIG. 29a being a plan view of a cover, FIG. 29b a plan view of a spacer, and FIG. 29c a plan view of a base plate.

FIGS. 29a to 29c are exploded plan views of the sensor chip 141.

FIG. 29c is a plan view of the base plate 125.

The spacer 144 shown in FIG. 29b (corresponds to the spacer 127 in Embodiment 9) is affixed to the top face of the base plate 125. The spacer 144 has a plurality of bumps 142a on the face on one side of its substantially rectangular shape. The cover 131 shown in FIG. 29a is affixed to the top face of the spacer 144.

In this embodiment, the sensor chip 141 is constituted by combining these members (the base plate 125, the spacer 144, and the cover 131).

Because of the above, when the sensor chip 141 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 11

Figure 31:
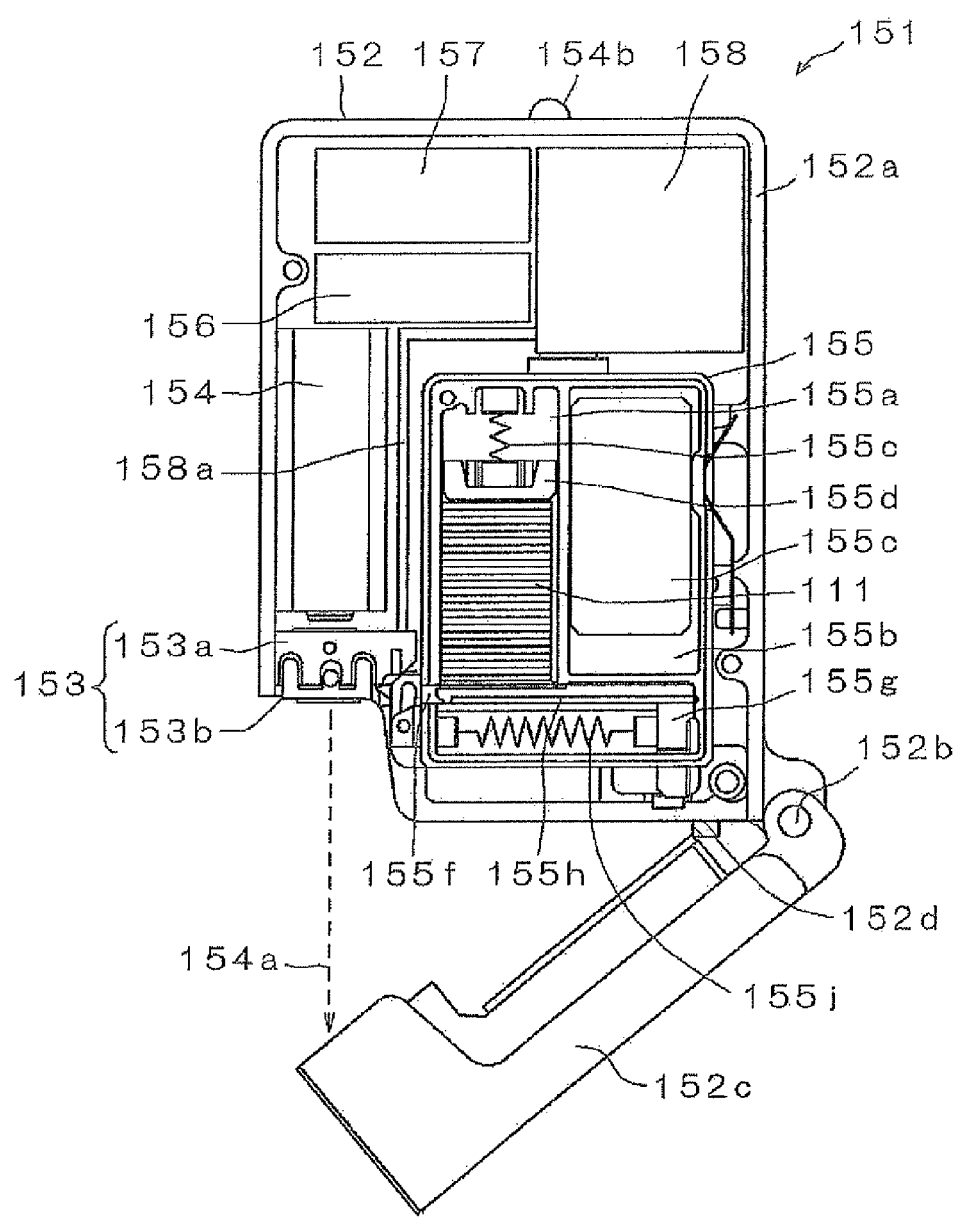
FIG. 31 is a part layout diagram of a blood test device pertaining to Embodiment 11 of the present invention.

FIG. 31 is a part layout diagram of a blood test device 151 that performs blood glucose measurement and so forth using the sensor chips 111 and 141 given in Embodiments 9 and 10.

The blood test device 151 punctures the skin of a diabetes patient, etc., and tests the blood 3 that is squeezed out from this puncture. Therefore, there is no need to separately ready a puncture device for drawing out the blood 3 and a measurement device for measuring this blood 3 as in the past. Furthermore, the series of operations consisting of puncturing of the skin, blood collection, and measurement/testing can be performed all at once (one-step operation).

In FIG. 31, a housing 152 has a cuboid shape. A lid 152c is rotatably linked via a fulcrum 152b to the end of a main body 152a of the housing 152. The opening and closing of the lid 152c is detected by a sensor 152d mounted below the main body 152a. A puncture component 153 is provided at a lower corner of the main body 152a, and is configured by a top holder 153a and a bottom holder 153b so as to sandwich the above-mentioned sensor chip 111 or the sensor chip 141. In this embodiment, a case of using the sensor chip 111 will be described.

A laser puncture unit 154 (serving as a puncture component) is mounted opposite the puncture component 153. Instead of the laser puncture unit 154, a needle puncture unit may be used as the puncture component. A sensor unit 155 is disposed at a location adjacent to the laser puncture unit 154. The sensor unit 155 has a sensor chamber 155a and a drying chamber 155b. The sensor chips 111 are stacked and held in the sensor chamber 155a. The stacked sensor chips 111 are pressed downward by a pressing plate 155d by a spring 155c.

A desiccant 155e is held in the drying chamber 155b. An outlet 155f, from which the sensor chips 111 are conveyed, is formed in the lower corner of the sensor chamber 155a. The sensor chips 111 conveyed out of the outlet 155f are conveyed by a conveyance unit 155g. The conveyance unit 155g has a conveyor plate 155h and a spring 155j that biases the conveyor plate 155h toward its original state.

A high-voltage generator 156 that supplies high voltage to the laser puncture unit 154 is disposed above the laser puncture unit 154. An electrical circuit 157 is disposed above the high-voltage generator 156. A negative pressure section 158 is provided above the sensor unit 155. The negative pressure section 158 supplies negative pressure to a negative pressure chamber 153d (see FIG. 32) of the puncture component 153 via a negative pressure path 158a.

A puncture button 154b for emitting a laser beam 154a from the laser puncture unit 154 is provided to the upper lateral face of the main body 152a. When the puncture button 154b is depressed, the laser beam 154a is emitted from the laser puncture unit 154. The opening angle of the lid 152c is restricted to a specific angle in order to prevent the laser beam 154a from leaking to the outside. Therefore, safe operation can be ensured, with no leakage of the laser beam 154a to the outside.

Figure 32:
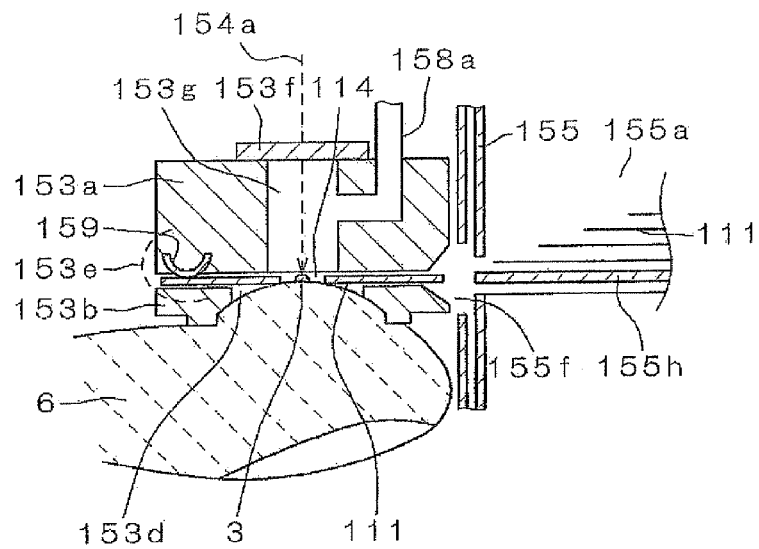
FIG. 32 is a cross section of the main components of the blood test device in FIG. 31.

FIG. 32 is a cross section of the main components near the puncture component 153 in the blood test device 151.

The puncture component 153 has the top holder 153a and the bottom holder 153b. The bottom holder 153b is biased to the top holder 153a side by a leaf spring 153e. A connector 159 is connected to the connection terminals 117a, 118a, 119a, and 120a (see FIG. 28) of the sensor chip 111 sandwiched between the top holder 153a and the bottom holder 153b, and sends signals to the electrical circuit 157.

A transparent member 153f is provided removably to the top face of the top holder 153a. A hole 153g is provided below the transparent member 153f. Therefore, the laser beam 154a emitted from the laser puncture unit 154 punctures the skin 6 by passing straight through the transparent member 153f, the hole 153g, the reservoir 114 of the sensor chip 111, and the negative pressure chamber 153d. This forms a puncture wound in the skin 6, from which the blood 3 seeps out.

The blood 3 that comes out of the skin 6 is taken in through the reservoir 114 of the sensor chip 111 shown in FIG. 28. After this, it is introduced into the supply path 115 by capillary action, and undergoes a chemical reaction with the reagent 24 placed on the detector 121 inside the supply path 115.

The result of this chemical reaction is sent through the connector 159 to the electrical circuit 157, the blood glucose value is measured, and this is displayed on a display component (not shown) provided to the front of the housing 152.

The electrical circuit 157 includes a measurement circuit that is the same as the measurement circuit 35 given in Embodiment 1 above, and a circuit that produces control signals for controlling the high-voltage generator 156 by a signal indicating that the puncture button 154b has been depressed.

When the blood glucose measurement is complete, the user causes any surplus blood 3a near the puncture wound formed by laser puncture to flow into the surplus blood reservoirs 113 of the sensor chip 111.

More specifically, the user takes the sensor chip 111 out of the blood test device 151, and touches the portion of the opening of the tiny gap formed by the lateral face on the long side of the sensor chip 111 so as to scrape it against the skin surface on which the surplus blood 3a remains. Consequently, the surplus blood 3a remaining on the skin is taken in and held inside the surplus blood reservoirs 113 through the tiny gap by capillary action. Thus, the user can use the used sensor chip 111 in place of a cotton ball or the like for wiping away the surplus blood 3a.

In this embodiment, the sensor chip that is mounted in the blood test device 151 is not limited to the sensor chip 111 shown in FIG. 28, and any of the sensor chips described above or below can of course be used.

Embodiment 12

Figure 34:
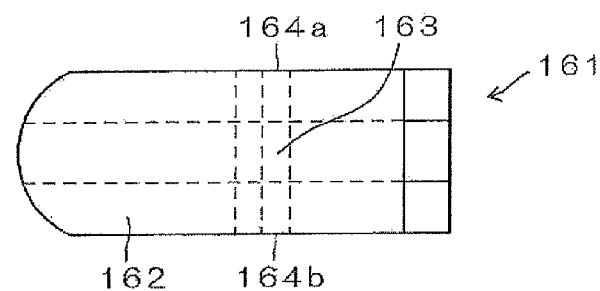
FIG. 34 is a plan view of the sensor chip in FIG. 33.

FIG. 34 is a plan view of a sensor chip 161 in Embodiment 12 (corresponds to the sensor chip 11 in Embodiment 1).

In this embodiment, a surplus blood reservoir 162 is provided over one entire lateral face of the substantially rectangular sensor chip 161, and a supply path 163 (corresponds to the supply path 21 in Embodiment 1) that goes through in between the two lateral faces is formed on the other lateral face. Therefore, the surplus blood 3a can be drawn in over one entire lateral face of the sensor chip 161, and the measurement-use blood 3 can be made to flow onto a specific detection electrode from either of the lateral faces of the sensor chip 161.

Figure 33:
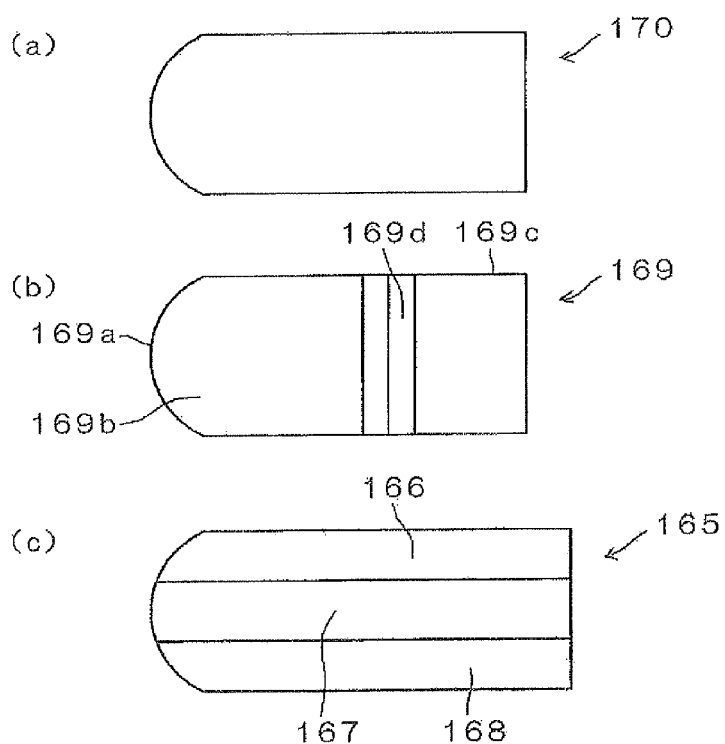
FIG. 33 consists of exploded plan views of the sensor chip pertaining to Embodiment 12 of the present invention, with FIG. 33a being a plan view of a cover, FIG. 33b a plan view of a spacer, and FIG. 33c a plan view of a base plate.

FIGS. 33a to 33c are exploded plan views of the sensor chip 161.

FIG. 33c is a plan view of a base plate 165. A detection electrode 166 (counter electrode), a detection electrode 167 (working electrode), and a detection electrode 168 (detecting electrode) are provided parallel to each other and along the lengthwise direction of the base plate 165, on the base plate 165.

When blood 3 flows from an inlet 164a that communicates with the supply path 163 (see FIG. 34), the detection electrode 168 becomes the electrode that detects the flow of the blood 3. On the other hand, when the blood 3 flows from the inlet 164b side that communicates with the supply path 153 (see FIG. 34), the detection electrode 166 becomes the electrode that detects the flow of the blood 3.

The spacer 169 shown in FIG. 33b (corresponds to the spacer 13 in Embodiment 1) is affixed to the top face of the base plate 165.

The spacer 169 has a concave face 169b, which forms the surplus blood reservoir 162, on one short side 169a of its substantially rectangular shape. The other short side 169c is provided with a groove 169d that forms the supply path 163 and passes through between the lateral faces. The cover 170 shown in FIG. 33a is affixed to the top face of the spacer 169.

No air hole is formed in the cover 170.

In this embodiment, the sensor chip 161 is constituted by combining these members (the base plate 165, the spacer 169, and the cover 170).

Because of the above, when the sensor chip 161 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 13

Figure 36:
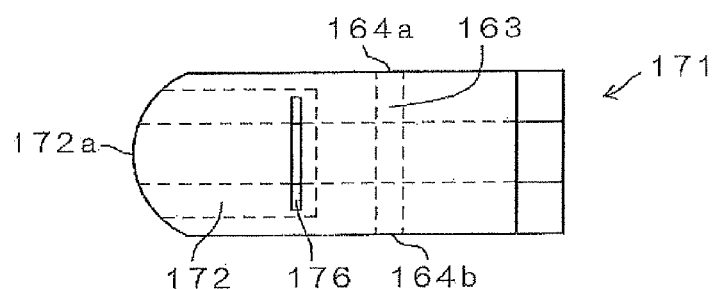
FIG. 36 is a plan view of the sensor chip in FIG. 35.

FIG. 36 is a plan view of a sensor chip 171 in Embodiment 13 (corresponds to the sensor chip 161 in Embodiment 12).

The sensor chip 171 in this embodiment differs from Embodiment 12 above in that a surplus blood reservoir 172 having a surplus blood inlet 172a is provided on only one short side of the substantially rectangular sensor chip 171. Therefore, the surplus blood 3a can be drawn in only from one short side of the sensor chip 171. Also, just as in Embodiment 12 above, the measurement-use blood 3 can be introduced from either of the lateral faces of the sensor chip 171.

Figure 35:
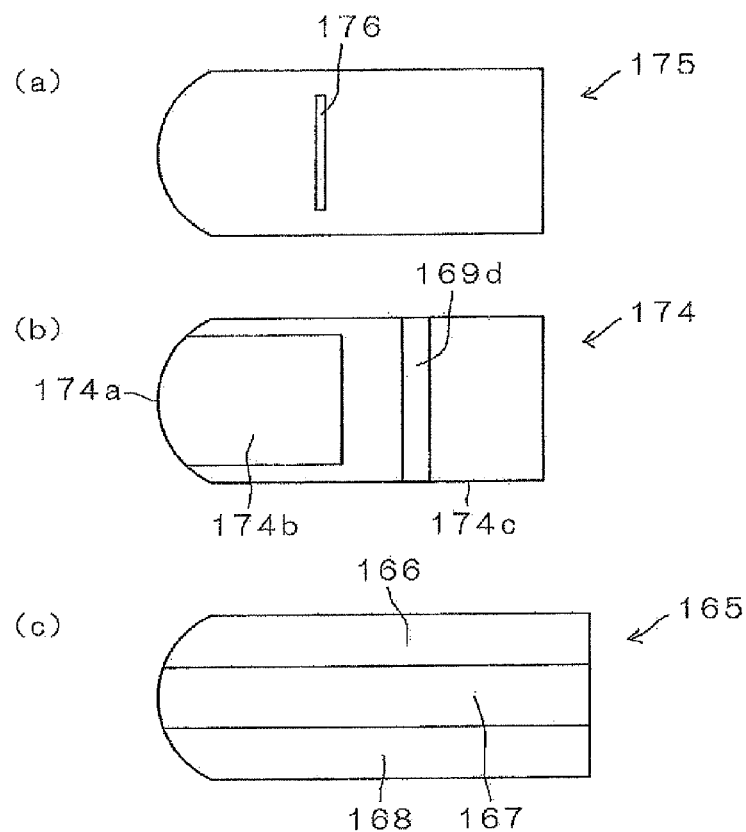
FIG. 35 consists of exploded plan views of the sensor chip pertaining to Embodiment 13 of the present invention, with FIG. 35a being a plan view of a cover, FIG. 35b a plan view of a spacer, and FIG. 35c a plan view of a base plate.

FIGS. 35a to 35c are exploded plan views of the sensor chip 171.

FIG. 35c is a plan view of the base plate 165. The spacer 174 shown in FIG. 35b (corresponds to the spacer 169 in Embodiment 12) is affixed to the top face of the base plate 165. With the spacer 174, a concave face 174b that forms the surplus blood reservoir 172 is formed at the portion excluding the two end portions of one short side 174a of the substantially rectangular shape. The groove 169d that forms the supply path 163 is provided on the long side 174c of the spacer 174, and passes through between the two lateral faces. The cover 175 shown in FIG. 33a is affixed to the top face of the spacer 174. A slit-shaped air hole 176 is formed at a location corresponding to the most interior part of the surplus blood reservoir 172.

In this embodiment, the sensor chip 171 is constituted by combining these members (the base plate 165, the spacer 174, and the cover 175).

Because of the above, when the sensor chip 171 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 14

Figure 38:
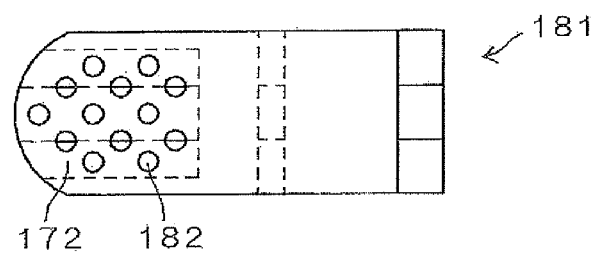
FIG. 38 is a plan view of the sensor chip in FIG. 37.

FIG. 38 is a plan view of a sensor chip 181 in Embodiment 14 (corresponds to the sensor chip 171 in Embodiment 13).

The sensor chip 181 in this embodiment differs from the sensor chip 171 in the shape of air holes 182 formed on the top face of the surplus blood reservoir 172.

Figure 37:
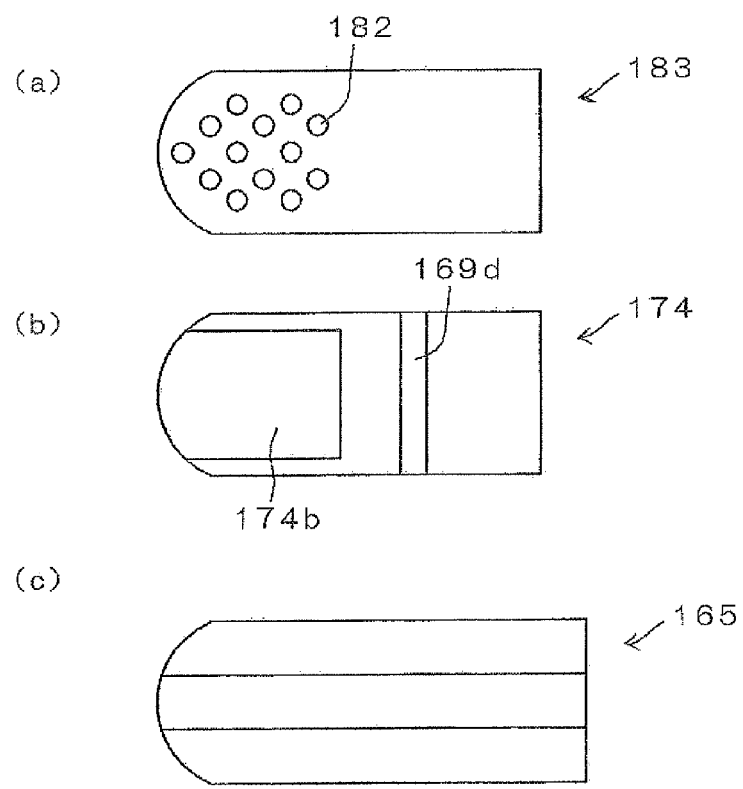
FIG. 37 consists of exploded plan views of the sensor chip pertaining to Embodiment 14 of the present invention, with FIG. 37a being a plan view of a cover, FIG. 37b a plan view of a spacer, and FIG. 37c a plan view of a base plate.

FIGS. 37a to 37c are exploded plan views of the sensor chip 181. FIG. 37c is a plan view of the base plate 165. The spacer 174 shown in FIG. 37b is affixed to the top face of the base plate 165. The cover 183 shown in FIG. 37a is affixed to the top face of the spacer 174. A plurality of air holes 182 are formed over the entire location corresponding to the surplus blood reservoir 172.

In this embodiment, the sensor chip 181 is constituted by combining these members (the base plate 165, the spacer 174, and the cover 183).

Because of the above, when the sensor chip 181 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 15

Figure 40:
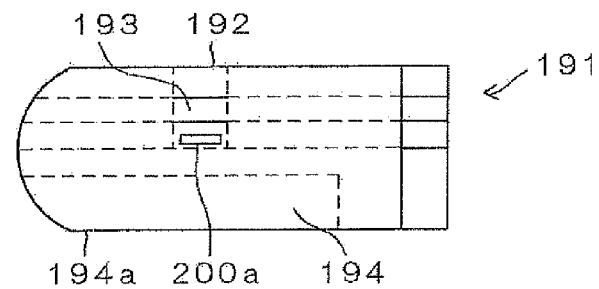
FIG. 40 is a plan view of the sensor chip in FIG. 39.

FIG. 40 is a plan view of a sensor chip 191 in Embodiment 15 (corresponds to the sensor chip 11 in Embodiment 1).

The sensor chip 191 in this embodiment is provided on one long side (the top) of the substantially rectangular shape with an inlet 192 (corresponds to the inlet 20 in Embodiment 1) for measurement-use blood 3, and a supply path 193 (corresponds to the supply path 21 in Embodiment 1) that communicates with the inlet 192. Also, it is provided on the other long side (the bottom) of the substantially rectangular shape with a surplus blood inlet 194a formed along substantially the entire long side, and a surplus blood reservoir 194 that communicates with this surplus blood inlet 194a.

Therefore, the measurement-use blood 3 can be introduced from one long side of the sensor chip 191. Also, since the surplus blood inlet 194a is provided along the entire other long side, a larger opening can be ensured for taking in the surplus blood 3a, which makes it easier to flow in.

Figure 39:
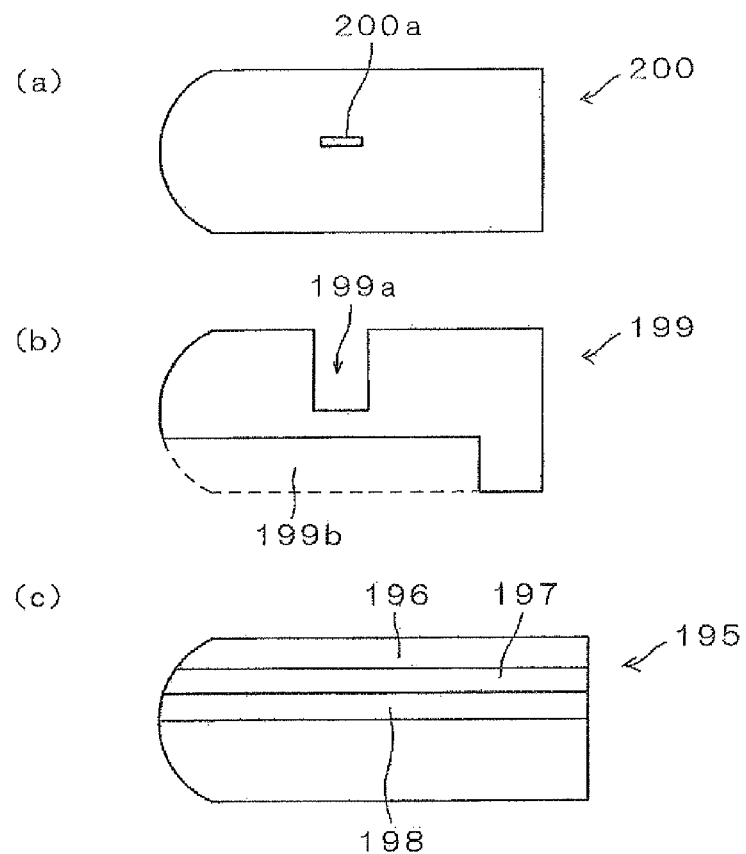
FIG. 39 consists of exploded plan views of the sensor chip pertaining to Embodiment 15 of the present invention, with FIG. 39a being a plan view of a cover, FIG. 39b a plan view of a spacer, and FIG. 39c a plan view of a base plate.

FIGS. 39a to 39c are exploded plan views of the sensor chip 191.

FIG. 39c is a plan view of the base plate 195. On the substantially rectangular base plate 195, a detection electrode 196 (C electrode), a detection electrode 197 (W electrode), and a de 198 are provided parallel to each other, in that order from one long side toward the center, in the long side direction. The detection electrodes 196, 197, and 198 are provided in between one long side and the center.

The spacer 199 shown in FIG. 39b is affixed to the top face of the base plate 195.

The spacer 199 is provided with a slit 199a that forms the supply path 193, from one long side toward the center. The spacer 199 is also provided with a cut-out 199b that forms the surplus blood reservoir 194, between the other long side and the center. The slit 199a and the cut-out 199b are formed independently at isolated locations.

The cover 200 shown in FIG. 39a is affixed to the top face of the spacer 199. The cover 200 is provided with an air hole 200a at a location corresponding to the most interior part of the supply path 193.

In this embodiment, the sensor chip 191 is constituted by combining these members (the base plate 195, the spacer 199, and the cover 200).

Because of the above, when the sensor chip 191 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Embodiment 16

Figure 42:
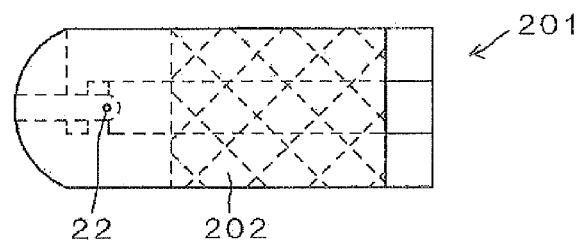
FIG. 42 is a plan view of the sensor chip in FIG. 41.

FIG. 42 is a plan view of a sensor chip 201 in Embodiment 16 (corresponds to the sensor chip 51 in Embodiment 3).

The sensor chip 201 in this embodiment differs from the embodiments given above in that a surplus blood suction member 202 serving as a surplus blood reservoir is affixed to the top or bottom face. Therefore, the surplus blood 3a can be drawn in and held inside the sensor chip 201 by touching the top of bottom face of the sensor chip 201 to the surplus blood 3a.

Figure 41:
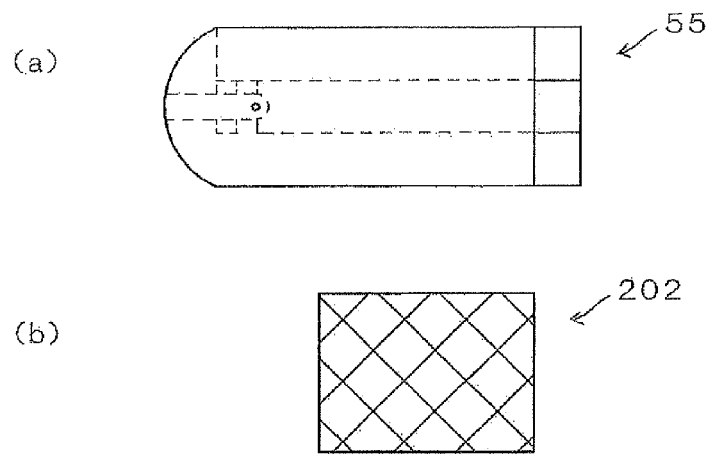
FIG. 41 consists of exploded plan views of the sensor chip pertaining to Embodiment 16 of the present invention, with FIG. 41a being a plan view of a cover, FIG. 41b a plan view of a spacer, and FIG. 41c a plan view of a substrate.

FIGS. 41a to 41c are exploded plan views of the sensor chip 201.

FIG. 41a is the blood measurement portion 55 from Embodiment 3 above (see FIG. 15). The blood measurement portion 55 has the base plate 43 shown in FIG. 14, the spacer 44 affixed to the top face of the base plate 43, and the cover 45 affixed to the top face of the spacer 44.

The surplus blood suction member 202 shown in FIG. 41b (used as an example of a surplus blood reservoir) is affixed to the top or bottom face of the blood measurement portion 55 constituted as above.

The surplus blood suction member 202 has a rectangular shape, and is affixed at a location that does not cover the air hole 22 (so that the air hole 22 will be exposed). A porous member such as filter paper can be used for this surplus blood suction member 202.

In this embodiment, the sensor chip 201 is constituted by combining these members (the blood measurement portion 55 and the surplus blood suction member 202).

Because of the above, when the sensor chip 201 in this embodiment is used, there is no need for the user to carry around tissues, cotton balls, or the like for wiping away surplus blood as in the past, and furthermore, when measurement is finished, the sensor chip that has drawn in surplus blood can be discarded. As a result, the same effects as in the above embodiments can be obtained, e.g., surplus blood can be easily dealt with, and work efficiency can be improved.

Features

The sensor chip of the present invention is a sensor chip that analyzes the components of a biological sample such as blood, and comprises a flat substrate, an inlet, a supply path, and detection electrodes. The inlet is provided to one end of this substrate, and it is through this inlet that the biological sample used for analysis flows in. The supply path communicates with this inlet, and it is through this supply path that the biological sample is introduced. The detection electrodes are provided to this supply path, and detect signals used for analysis. Surplus blood, which is extra biological sample that was not used in analysis, is drawn into the substrate, and there is a surplus blood reservoir for holding this surplus blood.

There is also provided a sensor chip in which the substrate has a suction member that draws in surplus blood that is extra biological sample that was not used in analysis.

The measurement device of the present invention is one that makes use of the above-mentioned sensor chip, and comprises a housing, a sensor insertion portion, a connector, a measurement circuit, and a display component. The sensor insertion portion is provided to one side of this housing, and allows a sensor chip to be inserted. The connector is provided to this sensor insertion portion. The measurement circuit is connected to this connector. The display component is connected to the output of this measurement circuit. The measurement circuit measures analysis data for the biological sample introduced into the sensor chip, and displays this result on the display component.

This allows the desired object to be attained.

Furthermore, the measurement device of the present invention comprises a housing, a sensor insertion portion, a connector, a measurement circuit, and a display component. The sensor insertion portion is provided to one side of the housing, and allows the sensor chip to be inserted. The connector is provided to this sensor insertion portion. The measurement circuit is connected to this connector. The display component is connected to the output of this measurement circuit. The connector has terminals for surplus blood detection electrodes that detect that surplus blood has been drawn into the sensor chip.

The blood test device of the present invention comprises a housing, a sensor insertion portion, puncture component, a connector, an electrical circuit, and a display component. The sensor insertion portion is provided to one side of the housing, and allows the mounting of the above-mentioned sensor chip used for analysis (including when there are surplus blood detection electrodes). The puncture component is provided at a location that is opposite or near the sensor insertion portion, and is provided in order to puncture the skin. The connector is provided to the sensor insertion portion. The electrical circuit is connected to this connector, and performs analysis of liquids and other such biological samples. The display component is connected to the output of this electrical circuit.

Consequently, the device is safer and easier for the user to use, and the desired object is realized.

Effect

As discussed above, with the present invention, there is no need for the user to carry around tissues, cotton balls, or the like for wiping away surplus blood as in the past, and furthermore, when measurement is finished, the sensor chip that has drawn in surplus blood can be discarded. As a result, surplus blood can be easily dealt with, and work efficiency can be improved.

With the sensor chip in the present invention, the inside of the surplus blood reservoir is either given a hydrophilic treatment or formed from a hydrophilic material, the area around the surplus blood reservoir is either given a water-repellency treatment or formed from a water-repellent material, and the surplus blood reservoir has a large enough volume. Therefore, once blood (the biological sample) has been held inside the sensor chip, it will not leak out from the sensor chip or adhere to the outside, so the device is safe to use.

INDUSTRIAL APPLICABILITY

The sensor chip pertaining to the present invention allows surplus blood to be dealt with easily, so it can be widely applied to blood testing and so forth in measurement devices, blood test devices, and the like.

REFERENCE SIGNS LIST 3 blood
3a surplus blood
11 sensor chip
12 base plate
13 spacer
13b cut-out
14 cover
15 substrate
17, 18, 19 detection electrode
20 inlet
21 supply path
23 detector
25 surplus blood reservoir

The invention claimed is:

1. A sensor chip for analyzing components of a biological sample, the sensor chip comprising:
   a substrate;
   a sample inlet provided to the substrate, said sample inlet configured to receive a part of the biological sample;
   a supply path provided to the substrate and being connected to the sample inlet, said supply path configured to receive the part of the biological sample from the sample inlet;
   detection electrodes provided to the supply path, said detection electrodes being configured to detect signals used for analysis of the part of the biological sample; and
   a surplus blood reservoir provided to the substrate and not being connected to the supply path, said surplus blood reservoir configured to hold a surplus of the biological sample, the surplus of the biological sample not including the part of the biological sample from which signals used for analysis are detected by the detection electrodes,
   wherein the substrate has a surplus blood inlet that is provided to an end of the substrate, the surplus of the biological sample being provided to the surplus blood inlet,
   wherein the surplus blood inlet draws the surplus of the biological sample into the surplus blood reservoir by capillary action,
   wherein the sample inlet is provided to one end face of the substrate, and
   wherein the surplus blood inlet is provided to an end face of the substrate that is different side from the end face where the sample inlet is provided.

2. The sensor chip according to claim 1,
   wherein the surplus blood reservoir has an opening on one or more faces of the substrate.

3. The sensor chip according to claim 1,
   wherein the volume of the surplus blood reservoir is greater than the volume of the supply path.

4. The sensor chip according to claim 1,
   wherein the volume of the surplus blood reservoir is no more than two thirds the volume of the substrate.

5. The sensor chip according to claim 1,
   wherein a plurality of the surplus blood inlets are provided.

6. The sensor chip according to claim 5,
   wherein the surplus blood inlets are disposed symmetrically in reference to the lengthwise center line of the substrate.

7. The sensor chip according to claim 5,
   wherein the plurality of surplus blood inlets that are provided are disposed at mutually adjacent locations.

8. The sensor chip according to claim 1,
   wherein a plurality of the surplus blood reservoirs are provided.

9. The sensor chip according to claim 8,
   wherein the plurality of surplus blood reservoirs that are provided are disposed symmetrically in reference to the lengthwise center line of the substrate.

10. The sensor chip according to claim 8,
    wherein the plurality of surplus blood reservoirs are formed in the same shape as one another.

11. The sensor chip according to claim 8,
    wherein the plurality of surplus blood reservoirs are formed in mutually different shapes.

12. The sensor chip according to claim 1,
    wherein the supply path and the surplus blood reservoir are formed by the same member,
    wherein the substrate is formed by laminating a base plate, a spacer, and a cover, and
    wherein the supply path and the surplus blood reservoir are formed in the same layer.

13. The sensor chip according to claim 12,
    wherein the supply path and the surplus blood reservoir are formed as respective separate spaces by the spacer.

14. The sensor chip according to claim 1,
    wherein the supply path and the surplus blood reservoir are formed in different layers, and
    wherein the substrate is formed by laminating a base plate, a spacer, a cover, and a surplus blood suction spacer.

15. The sensor chip according to claim 14,
wherein the supply path and the surplus blood reservoir are formed by separate members.
16. The sensor chip according to claim 1,
wherein a plurality of bumps are provided on the inside of the surplus blood reservoir.
17. The sensor chip according to claim 1,
wherein the substrate has a surplus blood detection electrode that detects blood that has flowed into the surplus blood reservoir.
18. The sensor chip according to claim 1,
wherein the sample inlet is provided to a first edge side of the substrate, and
wherein the surplus blood inlet is provided to a second edge on the sample inlet side.
19. The sensor chip according to claim 1,
wherein the sample inlet is provided to a first edge side of the substrate,
wherein the surplus blood inlet is provided to a second edge on the sample inlet side, and
wherein a plurality of bumps are formed on the inside of the surplus blood reservoir.
20. The sensor chip according to claim 1,
wherein the surplus blood inlet is provided on a first edge side of the substrate, and
wherein a measurement blood inlet is provided on a second edge side of the substrate.
21. The sensor chip according to claim 1,
wherein the surplus blood inlet is provided to an entire first edge of the substrate, and
wherein the sample inlet is provided in the approximate center of a second edge of the substrate.
22. The sensor chip according to claim 1,
wherein the surplus blood inlet is provided to an entire first edge of the substrate,
wherein a plurality of bumps are formed on the inside of the surplus blood reservoir, and
wherein there is further provided a supply path that passes through the substrate in between two opposite edges.
23. The sensor chip according to claim 1,
wherein the substrate has a substantially rectangular shape,
wherein the sample inlet is provided to a first short side of the substantially rectangular shape, and
wherein the surplus blood reservoir is a surplus blood suction member that is affixed to the upper or lower face of the substrate.
24. The sensor chip according to claim 1,
wherein the surplus blood inlet and its surrounding portion are given a water repellency treatment or formed by a water-repellent member.
25. The sensor chip according to claim 1,
wherein the volume of the surplus blood reservoir is at least three times greater than the volume of the supply path.
26. The sensor chip according to claim 1,
wherein the part of the biological sample received by the sample inlet is provided to the sample inlet separately from the surplus of the biological sample provided to be held by the surplus blood reservoir.
27. The sensor chip according to claim 1,
wherein the part of the biological sample received by the sample inlet is provided to the sample inlet separately from the surplus of the biological sample provided to surplus blood inlet.
28. The sensor chip according to claim 1,
wherein the substrate is formed by laminating a base plate, a spacer, and a cover,
wherein the spacer includes a slit, the slit forming the supply path,
wherein the spacer includes a pair of cut-outs, the pair of cut-outs forming the surplus blood reservoir,
wherein the slit is formed at a first edge side of the spacer, and
wherein the pair of cut-outs are formed at a second edge side of the spacer and a third edge side of the spacer, respectively, the second edge side and the third edge side being opposite edge sides of the spacer and being different than the first edge side.
29. A sensor chip for analyzing components of a biological sample, the sensor chip comprising:
a substrate;
a sample inlet provided to the substrate, said sample inlet configured to receive a part of the biological sample;
a supply path provided to the substrate and being connected to the sample inlet, said supply path configured to receive the part of the biological sample from the sample inlet;
detection electrodes provided to the supply path, said detection electrodes being configured to detect signals used for analysis of the part of the biological sample; and
a surplus blood reservoir provided to the substrate and not being connected to the supply path, said surplus blood reservoir configured to hold a surplus of the biological sample, the surplus of the biological sample not including the part of the biological sample from which signals used for analysis are detected by the detection electrodes,
wherein the substrate is formed by laminating a base plate, a spacer, a cover, a surplus blood suction spacer, and a surplus blood suction cover.
30. A measurement device, comprising:
a housing;
a sensor insertion portion that is provided to part of the housing and into which a sensor chip is inserted;
a connector that is provided to the sensor insertion portion;
a measurement circuit that is connected to the connector; and
a display component that is connected to the output of the measurement circuit and displays the result of measuring analysis data for a biological sample introduced to the sensor chip and measured with the measurement circuit,
wherein the sensor chip includes:
a substrate;
a sample inlet provided to the substrate, said sample inlet configured to receive a part of the biological sample;
a supply path provided to the substrate and being connected to the sample inlet, said supply path configured to receive the part of the biological sample from the sample inlet;
detection electrodes provided to the supply path, said detection electrodes being configured to detect signals used for analysis of the part of the biological sample;
a surplus blood reservoir provided to the substrate and not being connected to the supply path, said surplus blood reservoir configured to hold a surplus of the biological sample, the surplus of the biological sample not including the part of the biological sample from which signals used for analysis are detected by the detection electrodes; and
a surplus blood detection electrode that detects blood that flows into the surplus blood reservoir, and wherein there is further provided a terminal for the surplus blood detection electrode, the terminal being provided to the connector and detecting that surplus blood has been drawn into the sensor chip.

31. The measurement device according to claim 30, wherein the terminal for the surplus blood detection electrode also serves as the terminal for some or all of the connection terminals that connect to the detection electrodes used for analysis.

32. A blood test device, comprising:
a housing;
a sensor insertion portion that is provided to part of the housing and into which a sensor chip is inserted;
puncture component configured to puncture the skin, provided at or near a location that is opposite the sensor insertion portion;
a connector that is provided to the sensor insertion portion;
an electrical circuit that is connected to the connector and performs analysis of a biological sample; and
a display component that is connected to the output of the electrical circuit,
wherein the sensor chip includes:
   a substrate;
   a sample inlet provided to the substrate, said sample inlet configured to receive a part of the biological sample;
   a supply path provided to the substrate and being connected to the sample inlet, said supply path configured to receive the part of the biological sample from the sample inlet;
   detection electrodes provided to the supply path, said detection electrodes being configured to detect signals used for analysis of the part of the biological sample;
   a surplus blood reservoir provided to the substrate and not being connected to the supply path, said surplus blood reservoir configured to hold a surplus of the biological sample, the surplus of the biological sample not including the part of the biological sample from which signals used for analysis are detected by the detection electrodes; and
   a surplus blood detection electrode that detects blood that has flowed into the surplus blood reservoir, and
wherein there is further provided a surplus blood detection circuit that performs detection of surplus blood taken into the sensor chip.

33. A sensor chip for analyzing components of a biological sample, the sensor chip comprising:
a substrate;
a sample inlet provided to the substrate, said sample inlet configured to receive a part of the biological sample;
a supply path provided to the substrate and being connected to the sample inlet, said supply path configured to receive the part of the biological sample from the sample inlet;
detection electrodes provided to the supply path, said detection electrodes being configured to detect signals used for analysis of the part of the biological sample; and
a surplus blood reservoir provided to the substrate and not being connected to the supply path, said surplus blood reservoir configured to hold a surplus of the biological sample, the surplus of the biological sample not including the part of the biological sample from which signals used for analysis are detected by the detection electrodes,
wherein the substrate is formed by laminating a base plate, a spacer, a cover, a surplus blood suction spacer, and a surplus blood suction cover,
wherein the spacer includes a slit, the slit forming the supply path,
wherein the surplus blood suction spacer includes a pair of cut-outs, the pair of cut-outs forming the surplus blood reservoir, and
wherein the spacer and the surplus blood suction spacer are separated by the cover.

* * * * *